(12) United States Patent
Iwayama et al.

(10) Patent No.: US 7,199,070 B2
(45) Date of Patent: Apr. 3, 2007

(54) CONVERSION CATALYST FOR ETHYLBENZENE CONTAINING XYLENES AND PROCESS FOR CONVERTING ETHYLBENZENE CONTAINING XYLENES BY USING CATALYST

(75) Inventors: Kazuyoshi Iwayama, Nagoya (JP); Hiroshi Konta, Mie-ken (JP); Masatoshi Watanabe, Tajimi (JP)

(73) Assignee: Toray Industries, Inc., Tokyo (JP)

( * ) Notice: Subject to any disclaimer, the term of this patent is extended or adjusted under 35 U.S.C. 154(b) by 177 days.

(21) Appl. No.: 10/885,314

(22) Filed: Jul. 7, 2004

(65) Prior Publication Data
US 2005/0010074 A1 Jan. 13, 2005

(30) Foreign Application Priority Data

| Jul. 8, 2003 | (JP) | ............................. 2003-193267 |
| Sep. 5, 2003 | (JP) | ............................. 2003-313585 |

(51) Int. Cl.
*B01J 29/06* (2006.01)
*B01J 29/068* (2006.01)

(52) U.S. Cl. ............................ 502/66; 502/60; 502/63; 502/64; 502/69; 502/71; 502/73; 502/74; 502/77

(58) Field of Classification Search ................ 502/60, 502/63, 64, 66, 69, 71, 73, 74, 77
See application file for complete search history.

(56) References Cited

U.S. PATENT DOCUMENTS

| 3,856,871 | A |  | 12/1974 | Haag et al. ............ 260/668 A |
| 4,159,282 | A |  | 6/1979 | Olson et al. ................ 585/481 |
| 4,163,028 | A |  | 7/1979 | Tabak et al. ................ 585/481 |
| 4,899,011 | A |  | 2/1990 | Chu et al. ................... 585/481 |
| 4,923,835 | A |  | 5/1990 | Travers et al. ................ 502/66 |
| 5,290,932 | A | * | 3/1994 | Dingerdissen et al. ...... 544/178 |
| 5,672,796 | A | * | 9/1997 | Froment et al. ............ 585/419 |
| 5,877,374 | A |  | 3/1999 | Nacamuli et al. ........... 585/489 |
| 6,028,238 | A |  | 2/2000 | Beck et al. ................. 585/481 |
| 6,051,520 | A | * | 4/2000 | Wu et al. ...................... 502/60 |
| 6,051,744 | A |  | 4/2000 | Nacamuli et al. ........... 585/481 |
| 6,462,248 | B1 | * | 10/2002 | Nakatani et al. ............ 585/475 |

FOREIGN PATENT DOCUMENTS

| EP | 0 307 113 A1 | 3/1989 |
| EP | 0 500 413 A1 | 8/1992 |
| EP | 1 186 584 A | 3/2002 |
| JP | 49-46606 | 5/1974 |
| JP | 50-53335 | 5/1975 |
| JP | 55-394 A | 1/1980 |
| JP | 57-200319 A | 12/1982 |
| JP | 62-169736 A | 7/1987 |

* cited by examiner

*Primary Examiner*—Elizabeth D. Wood
(74) *Attorney, Agent, or Firm*—Kubovcik & Kubovcik

(57) ABSTRACT

A catalyst in which X-ray diffraction intensity ratio of the crystal lattice plane spacing d-value of 0.196±0.002 nm to the crystal lattice plane spacing d-value of 0.386±0.008 nm is in a range from 7:100 to 35:100 and a process for making the catalyst to contact with ethylbenzene containing xylenes in the presence of hydrogen.

10 Claims, 13 Drawing Sheets

X-ray diffraction pattern (embodiment 1, MFI-type zeolite)

Figure 2  FE-SEM observation view, of 10,000 power (embodiment 1, MFI-type zeolite)

Figure 3  X-ray diffraction pattern (hydrous alumina)

Figure 4  X-ray diffraction pattern (embodiment 1, catalyst A)

Figure 5  X-ray diffraction pattern (α-alumina)

Figure 6   X-ray diffraction pattern (comparative example 1, catalyst B)

Figure 7  X-ray diffraction pattern (comparative example 2, catalyst C)

X-ray diffraction pattern (embodiment 2, catalyst D)

FE-SEM observation view, of 10,000 power (embodiment 5, MFI-type zeolite)

FE-SEM observation view, of 10,000 power (embodiment 8, MFI-type zeolite)

FE-SEM observation view, magnified by 100,000 times (embodiment 9, MFI-type zeolite)

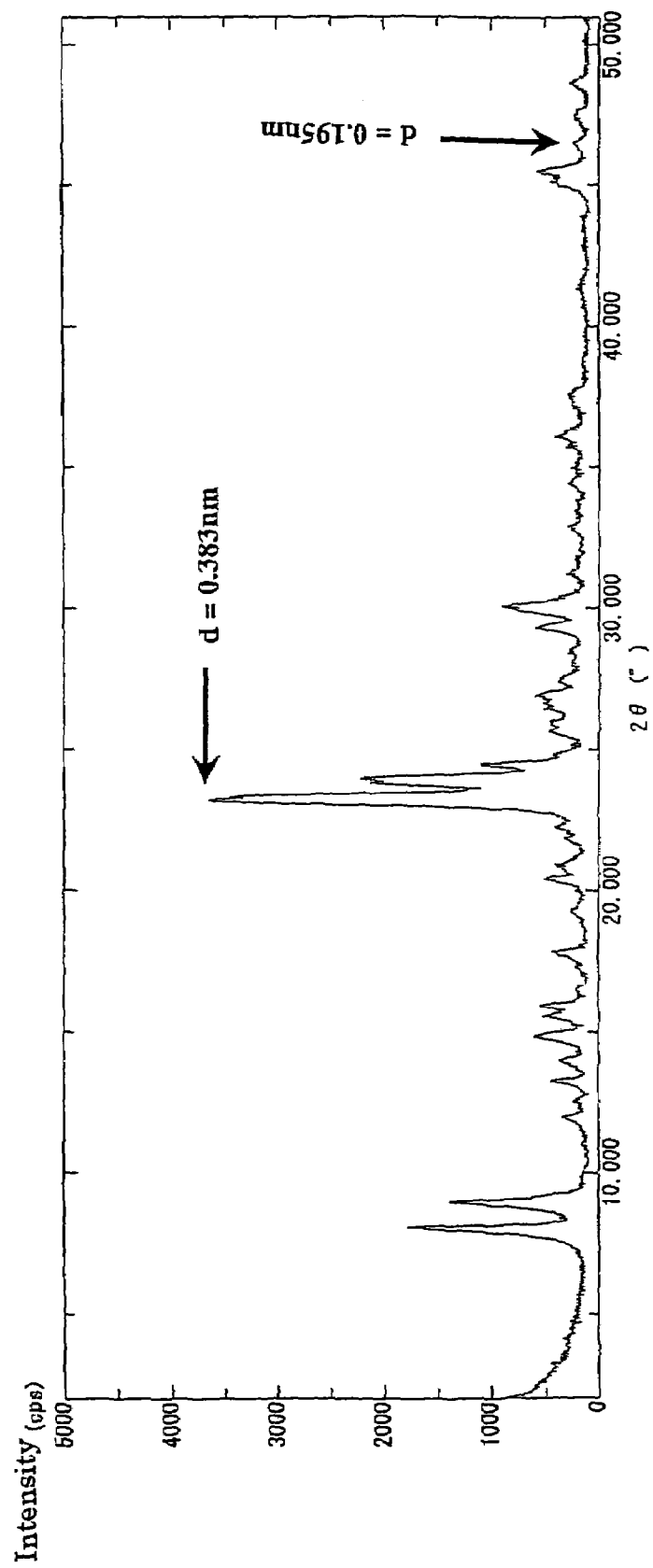
Figure 12   X-ray diffraction pattern (comparative example 3, catalyst K)

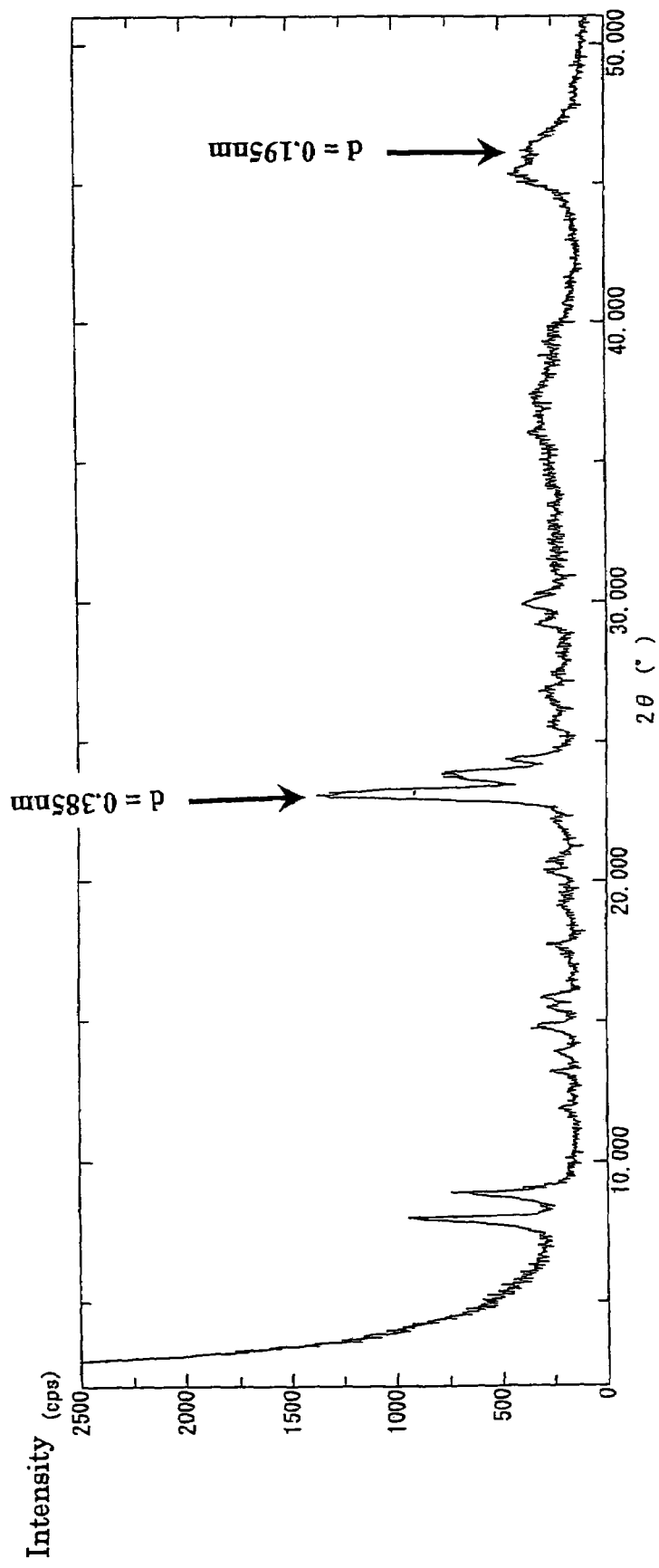
Figure 13  X-ray diffraction pattern (embodiment 36, catalyst U)

CONVERSION CATALYST FOR ETHYLBENZENE CONTAINING XYLENES AND PROCESS FOR CONVERTING ETHYLBENZENE CONTAINING XYLENES BY USING CATALYST

BACKGROUND OF THE INVENTION

The present invention relates to a conversion catalyst for ethylbenzene containing xylenes and a conversion process by using the catalyst, more particularly, a process in which ethylbenzene containing xylenes are made to contact with a specific catalyst in the presence of hydrogen, thus effecting dealkylation of ethylbenzene mainly into benzene and at the same time attaining isomerization of ortho-xylene and/or meta-xylene into para-xylene.

Of xylene mixtures, para-xylene is now in particular an industrially important product. The demand of para-xylene has remarkable increase as a crude raw material for polyester, a synthetic fiber. It is expected that para-xylene will continue to have such increase in the demand. Ortho-xylene and meta-xylene which are xylene isomers other than para-xylene are extremely lower in the demand than para-xylene, thus making it industrially important to convert them into para-xylene.

Since individual isomers of xylene and ethylbenzene are close in their boiling point, it is practically impossible to separate para-xylene through distillation method. Thus, low-temperature separation and adsorption separation processes are used for this purpose. The low-temperature separation process is restricted in recovery of para-xylene for the para-xylene recovery rate per one pass due to eutectic point, thus resulting in relatively high concentrations of para-xylene in raffinate fluid after recovery of para-xylene. In the low-temperature separation process the recovery rate of para-xylene per one pass can be improved with the high concentration of para-xylene contained in the supplied raw material.

In contrast, the adsorption separation process is able to recover para-xylene at 100% for one pass. Namely, the concentration of para-xylene in raffinate fluid after the adsorption and separation is extremely low or it can be reduced to almost zero. However, in this process, it is ethylbenzene that inhibits most the separation of para-xylene among C8 aromatic hydrocarbon mixtures. Thus, the reduced concentration of ethylbenzene in a raw material supplied for adsorption and separation makes it possible to improve the adsorption and separation function of para-xylene and increase the concentration of para-xylene in the raw material supplied, thereby improving the capacity of producing para-xylene in the same facility for adsorption and separation.

Therefore, raw materials for xylene to be supplied in the separation process should be those in which the concentration of ethylbenzene is kept as low as possible and the concentration of para-xylene in xylene kept as high as possible by which the concentration of para-xylene can be kept high in C8 aromatic hydrocarbon mixtures.

In general, industrially available xylene raw materials are reformed xylenes which are obtained through reformation of naphtha and subsequent aromatic extraction and/or fraction or cracked xylenes which are obtained by subjecting decomposite gasoline (by-product of thermal decomposition of naphtha) to aromatic extraction and/or fraction. Cracked xylenes are characterized by two-times higher concentration of ethylbenzene than that of reformed xylenes, a representative ingredient of which is shown in the table below.

TABLE

| Ingredients | Ingredients of xylene | |
|---|---|---|
| | reformed | cracked |
| Ethylbenzene | 18 weight % | 39 weight % |
| Para-xylene | 19 | 13 |
| Meta-xylene | 42 | 32 |
| Ortho-xylene | 21 | 16 |

As shown in the above, in general, xylene mixtures have a substantial quantity of ethylbenzene. Failure in removing ethylbenzene by any means would result in an undesirable situation where ethylbenzene accumulates after repetition of separation and isomerization steps, thus resulting in a higher concentration of ethylbenzene. Under these circumstances, reformed xylenes lower in the concentration of ethylbenzene are now used as a preferable source as freshly supplied raw materials. However, in recent years when a limited availability of petroleum has caught attention, reevaluation is made for thermally cracked xylenes as another xylene source. In any case, it is necessary to reduce the concentration of ethylbenzene, for which several processes have been proposed and some of them have been actually done on an industrial scale. These processes can be roughly classified into a process in which ethylbenzene is separated as it is and another process in which ethylbenzene is converted into other useful compounds through reactions.

Distillation is a process for separation of ethylbenzene. In this process, ultra-precision distillation is needed due to a small difference between the boiling point of ethylbenzene and that of xylene, thus requiring a great amount of investment for commercial production facilities and making the operational cost higher and economically unfavorable. There is another presented process by which adsorption and separation process is employed to separate ethylbenzene. This process is, however, not well satisfactory in the separation function.

Other processes for removing ethylbenzene include those for converting ethylbenzene into useful ingredients. The representative processes are shown below:

(1) a process for converting ethylbenzene into xylene (for example, refer to Japanese Patent No. 1974-46606 (the embodiment 3 on page 3), (2) a process for converting ethylbenzene into benzene and diethylbenzene through disproportionate reaction (for example, refer to Japanese Patent No. 1978-41657 (on 32nd–33rd line, 19th column, page 10) and (3) a process for converting ethylbenzene into benzene and ethane through dealkylation reaction (for example, refer to Japanese Patent Laid-Open No. 1982-200319 (embodiments from 2 to 4 on pages from 7 to 8).

Of the above process, the process (1) for converting ethylbenzene into xylene indispensably needs platinum, a quite expensive precious metal, to be contained in a catalyst. Further, conversion of ethylbenzene into xylene needs the presence of non-aromatic ingredients such as naphthene and paraffin in view of reaction mechanism, with the concentrations of such ingredients in the obtained product ranging from several to 10+several percentages. The process is also controlled for conversion of ethylbenzene by thermodynamic equilibrium and therefore restricted thereby. These matters are disadvantages of this process.

The above process (2) is for converting ethylbenzene into benzene and diethylbenzene through the disproportionate reaction. Benzene produced by the process is then hydrogenated to cyclohexane, a greatly-demanded raw material for nylon, a synthetic fiber, whereas diethylbenzene is hardly demanded and must be further converted into a useful compound, making diethylbenzene less favorable in an economic point of view.

Under these circumstances, the process (3) for converting ethylbenzene into benzene and ethane through dealkylation reaction has become predominant in recent years.

When ethylbenzene is effected dealkylation from a raw material of xylene isomer containing ethylbenzene to convert to benzene and then proceeding isomerization of ortho-xylene and meta-xylene to para-xylene, it is preferable to make the conversion of ethylbenzene as high as possible for the reduction of the cost of the separation of para-xylene. It is also preferable to reduce the loss of xylene as little as possible for reducing the original unit for the production of para-xylene and accordingly for lowering the cost of para-xylene production. From this point of view, an attempt of using zeolite, the crystallite size of which is greater than 1 micron (for example, Japanese Patent No. 1987-56138 (embodiments from 4 through 6 on page 10 and 11)), an attempt of reducing the diffusion speed of ortho-xylene (for example, Japanese Patent No.1996-16074 (the embodiment on page 5 through page 7)) and an attempt of using zeolite which has extremely high silica/alumina mole ratio of 500 or higher (for example, U.S. Pat. No. 4,163,028 (embodiments of 1 and 3 on page 14)) were done.

However, in these attempts, the loss of xylene is still high in relation to the conversion to ethylbenzene. Further, an attempt of decreasing the loss of xylene and increasing the conversion to ethylbenzene is not able to keep the isomerization of ortho-xylene and meta-xylene to para-xylene sufficiently high.

SUMMARY OF THE INVENTION

The purpose of the present invention is to provide a conversion catalyst for ethylbenzene containing xylenes and a process for using the catalyst, more particularly, a process for treating ethylbenzene containing xylenes to effect hydrogenation and dealkylation of ethylbenzene into benzene and ethane at a high level and also for reducing the loss of xylene occurring on isomerization of ortho-xylene and meta-xylene into para-xylene.

In order to attain the above purpose, the invention is comprised of the following: a conversion catalyst for ethylbenzene containing xylenes inclusive of MFI-type zeolite and alumina in which the X-ray diffraction intensity ratio of the crystal lattice plane spacing d-value of $0.196\pm0.002$ nm assigned to alumina to the crystal lattice plane spacing d-value of $0.386\pm0.008$ nm assigned to MFI-type zeolite is in a range from 7:100 to 35:100 as well as a process for converting ethylbenzene containing xylenes by making ethylbenzene containing xylenes to contact with the catalyst.

BRIEF DESCRIPTION OF THE DRAWINGS

FIG. 12 is an X-ray diffraction pattern of the catalyst K obtained in the comparative example 3; and FIG. 13 is an X-ray diffraction pattern of the catalyst U obtained in the embodiment 36.

DESCRIPTION OF THE PREFERRED EMDOBIMENTS

Figure 1:
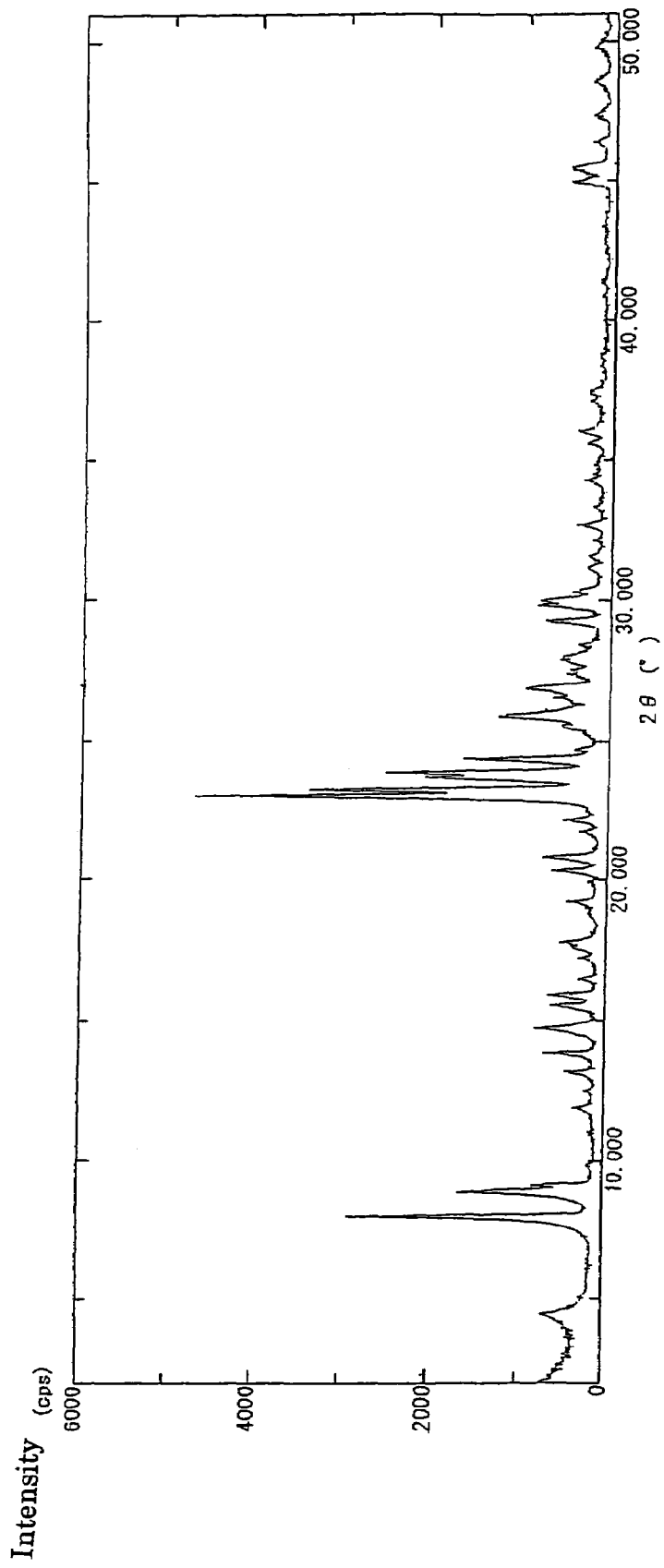
FIG. 1 is an X-ray diffraction pattern of MFI-type zeolite obtained in the embodiment 1.

Raw materials to be used in the invention include reformed xylene which is reformed by allowing naphtha obtained through petroleum refinery to contact with a catalyst and subjecting the naphtha to aromatic extraction and/or fraction; or cracked xylene which is obtained by subjecting cracked gasoline, a by-product of thermal decomposition of naphtha to aromatic extraction and/or fraction. Both of the reformed xylene and cracked xylene are xylene isomer mixtures which contain ethylbenzene.

Since these ethylbenzene containing xylene isomer mixtures contain para-xylene at the concentration close to the equilibrium concentration, the mixtures are firstly transferred to a separation step of para-xylene to separate para-xylene. Raffinate ingredients with lower concentration of para-xylene are then transferred to an isomerization step to perform conversion of ethylbenzene and isomerization reaction to para-xylene at the same time to remove the ingredients with higher boiling point than xylene and those with lower boiling point than xylene by fractioning. Thereafter, with the newly supplied raw material, the raffinate ingredients are again transferred to the separation step of para-xylene to separate para-xylene and raffinate with low concentration of para-xylene is recycled. Further, in recent years, an attempt has been made in which xylene isomer mixtures containing fresh ethylbenzene are made to contact with a catalyst in advance, thus causing hydrogenation and dealkylation of ethylbenzene into benzene ethane to reduce the concentration of ethylbenzene, in order to increase the concentration of para-xylene in the supplied liquid to be supplied to the para-xylene separation step and also effectively separate para-xylene. In this case, there are two processes available for attaining this purpose, namely a process in which xylene isomer mixtures containing fresh ethylbenzene are made to contact with a catalyst outside a loop during which raffinate ingredients after separation of para-xylene are recycled for the isomerization; and another process in which raffinate ingredients after the separation of para-xylene is directly supplied to an isomerization catalyst present in a loop during which the raffinate ingredients are recycled for the isomerization. They are both preferably used.

Zeolite to be used in the invention is MFI-type zeolite. MFI-type zeolite is characterized by having the X-ray diffraction pattern shown in the table below. The X-ray diffraction pattern is determined by a process in which irradiation of copper K-α ray is recorded by the use of a recorder-equipped Geiger counter spectroscope to obtain diffraction patterns.

TABLE

X-ray diffraction pattern of MFI-type zeolite

| Lattice plane spacing d(nm) | Relative intensity ($I/I_0$) |
|---|---|
| 1.12 ± 0.02 | S |
| 1.01 ± 0.2 | S |
| 0.98 ± 0.02 | M |
| 0.637 ± 0.01 | W |
| 0.600 ± 0.01 | W |
| 0.571 ± 0.01 | W |
| 0.558 ± 0.01 | W |
| 0.437 ± 0.008 | W |
| 0.427 ± 0.008 | W |
| 0.386 ± 0.008 | VS |
| 0.382 ± 0.008 | VS |
| 0.375 ± 0.008 | S |
| 0.372 ± 0.008 | S |
| 0.366 ± 0.005 | M |
| 0.300 ± 0.005 | M |
| 0.200 ± 0.005 | W |

In the table, the relative intensity (100 $I/I_0$) is expressed as follows: VS = very strong, S = strong, M = moderately strong and W = weak.

MFI-type zeolite can be obtained by the ZSM-5 synthetic process as shown in Japanese Patent No. 1971-10064 in which tetrapropylammonium hydroxide is added to aqueous reaction mixtures to synthesize the zeolite, the TSZ synthetic process as shown in Japanese Patent No. 3-45010 in which the zeolite is synthesized from aqueous reaction mixtures practically made up of inorganic reaction materials, or the pentasil-type zeolite synthetic process as disclosed in Japanese Patent No. 60-35284 in which aliphatic carboxylic acids or their derivatives are added to aqueous reaction mixtures to synthesize. Of these MFI-type zeolites, MFI-type zeolite which can be preferably used in the invention is zeolite having the crystalline major axis and minor axis in a range from 0.7 to 2.5 micron and silica/alumina (hereinafter abbreviated as "$SiO_2/Al_2O_3$") mole ratio from 30 to 55. More preferable MFI-type zeolite is that having the crystalline major axis and minor axis in a range from 1 to 2.5 micron and $SiO_2/Al_2O_3$ mole ratio from 35 to 45. Catalysts prepared from MFI-type zeolite, whose crystallite is smaller than 1 micron or more particularly smaller than 0.5 micron, will result in a greater loss of xylene, on conversion of ethylbenzene containing xylenes, mainly due to transalkylation occurred in methyl group of side chains of xylenes or in ethyl group of side chains of ethylbenzene. Such transalkylation may result in increasing of an area of extra-crystalline surface due to a smaller size of the crystallite of MFI-type zeolite and occur at solid acid points on the extra-crystalline surface. The extra-crystalline surface is considered to be different from the interior of fine pores of MFI-type zeolite but a free space, thus easily causing transalkylation, which is a bimolecular reaction. Crystallite greater than 2.5 micron will reduce the reaction activity, which may be due to a difficult arrival of reaction molecules at deeper areas of the crystallite according to a greater size of the crystallite of MFI-type zeolite, thus resulting in a lower utilization of fine pore space. In contrast, decreased $SiO_2/Al_2O_3$ mole ratio of MFI-type zeolite to 35 or further to 30 or lower will increase the loss of xylenes, which may be due to increased solid acid points on the out-surface of crystalline which will then augment the transalkylation activity of methyl group. Increased $SiO_2/Al_2O_3$ mole ratio of MFI-type zeolite to 45 or further to 56 or more will decrease the dealkylation activity of ethylbenzene or the isomerization activity of xylene. The decrease may be due to decrease in the solid acid points of zeolite according to increased $SiO_2/Al_2O_3$ mole ratio of MFI-type zeolite to 45 or further 55 or greater.

To be surprised, however, in the case of MFI-type zeolite having crystalline major axis and minor axis from 0.03 to 0.7 micron and silica/alumina mole ratio from 18 to 30, it has been found that in particular inclusion of strontium or barium in the zeolite results in a remarkable suppression of transalkylation on side chains of methyl group of xylene or side chains of ethyl group of ethylbenzene. This finding is estimated due to a greater ion radius of strontium or barium than that of magnesium or calcium, all of which are an alkaline-earth metal, thereby selectively reducing solid acid points on the extra-crystalline surface interior of fine pores.

Japanese Patent No.1971-10064 described the ZSM-5 synthetic process using tetrapropylammonium hydroxide, an organic compound containing nitrogen compound, more particularly, described in lines from 8th to 11th on the column 5 that "the compound was microscopically found to be composed of small crystals (about 1 micron) and some gel particles". It was also described in the embodiment 2 that the ZSM-5 having $SiO_2/Al_2O_3$ mole ratio of 31.1 was composed of very fine crystals (about 1 micron), in association with some gel particles.

A decrease in $SiO_2/Al_2O_3$ mole ratio in the presence of organic compound containing nitrogen will result in an increased crystal distortion according to crystalline growth because of the presence of bulky organic compound containing nitrogen at a cation exchange site. As the result, the crystallite can not grow bigger, with the average crystallite size of less than 1 micron, for example, 0.5 micron in most cases. In contrast, EP26,963A1 described that the ZSM-5 zeoltie having the average crystallite size from 1 to 2 micron was obtained in the condition where $SiO_2/Al_2O_3$ mole ratio was 180 or higher. This was because a high $SiO_2/Al_2O_3$ mole ratio resulted in a fewer cation exchange sites. Therefore, a fewer number of organic matter-containing cations present in a cation exchange site was considered to result in less distortion during the crystal growth and a greater size of the crystal.

The process for synthesizing MFI-type zeolite which is used preferably in the invention, namely, having the crystalline major axis and minor axis from 0.7 to 2.5 micron and silica/alumina mole ratio from 30 to 55 can be favorably carried out in the absence of organic compound containing nitrogen. It is considered that the absence of organic compound containing nitrogen in the course of crystal growth can make the crystal distortion smaller and retain the larger crystal size for some time in spite of a smaller $SiO_2/Al_2O_3$ mole ratio.

Crystallite size of zeolite can be easily determined by a field emission scanning-type electron microscope (FE-SEM) and others. The MFI-type zeolite of the present invention may have the crystalline major axis and minor axis in a range from 0.7 to 2.5 micron. The "average" crystallite size is described to the effect that the sample (zeolite) has the crystalline major axis and minor axis ranging from 0.7 to 2.5 micron at 50% or greater, preferably at 70% or greater. The silica/alumina mole ratio can be easily determined by various processes such as atomic absorption spectrometry method, fluorescent X-ray diffraction and ICP (inductively coupled plasma) emission spectrochemical analysis.

In addition, any zeolite synthesized either in the presence or absence of organic compound containing nitrogen can be used in the process for synthesizing the preferably used zeolite for the present invention, which has major axis and minor axis ranging from 0.03 to 0.7 micron and silica/alumina mole ratio from 18 to 30; however the zeolite synthesized in the absence of organic compound containing nitrogen is preferably used. Zeolite synthesized in the presence of organic compound containing nitrogen contains organic nitrogen cation. Such zeolite is usually calcinated in the presence of oxygen to remove organic nitrogen cation, during which the zeolite may be often affected by crystal lattice defect. The crystal lattice defect may easily cause decomposition in association with the reaction of aromatic compounds with a conversion catalyst.

Synthesized zeolite is usually available in a powder form. It is important to mold zeolite into a substantially large size for using it as an industrial catalyst. Hydrogenated ingredients must be supported on a catalyst so that ethylbenzene can be hydrogenated and dealkylated to mainly benzene ethane, which is the main subject of the present invention. The hydrogenated ingredients include rhenium, platinum and nickel. In particular, rhenium is lower in the nuclear hydrogenation reaction of phenyl group and can be favorably used in the invention. For the purpose of effectively attaining the hydrogenation and dealkylation reaction of ethylbenzene into benzene and the isomerization reaction of ortho-xylene and meta-xylene into para-xylene on a catalyst, it is important to provide a uniform dispersion of MFI-type zeolite crystals in catalyst particles, and also important to provide a uniform support of hydrogenated ingredients in catalyst particles. For accomplishing the purpose, zeolite powder is mixed with an inorganic oxide powder and then diluted. A diluted inorganic oxide favorably used in the present invention is alumina. Alumina is available as boehmite, boehmite gel, gypsite, bialite, norstrandite, diaspore and amorphous alumina gel. Any types of alumina may be used in the invention. A particularly preferable diluted alumina is boehmite having the lattice plane spacing that can be determined by X-ray diffraction as shown in the table below. It is also possible to add other inorganic oxides to the boehmite, whenever necessary.

TABLE

X-ray diffraction pattern of diluted alumina

| Lattice plane spacing d(nm) | relative intensity ($I/I_0$) |
|---|---|
| 0.627 ± 0.02 | M |
| 0.317 ± 0.02 | M |
| 0.234 ± 0.02 | M |
| 0.185 ± 0.01 | M |

It is well known that alumina is converted into γ-, η-, δ- or α-type alumina depending on calcinations course. Boehmite, the diluted alumina favorably used in the present invention, undergoes structural changes in the course of preparing the catalyst related to the invention, thus resulting in changes in the lattice plane spacing. Alumina in the form of catalyst favorable in the invention is that having the lattice plane spacing d-value of 0.196±0.002 nm. In particular, a catalyst whose X-ray diffraction intensity ratio of the lattice plane spacing d-value of 0.196±0.002 nm assigned to alumina to the lattice plane spacing d-value of 0.386±0.008 nm assigned to MFI-type zeolite in the catalyst ranges from 7:100 to 35:100 should be used in the invention. The X-ray diffraction intensity ratio can be determined as follows: the catalyst is ground into a powder and irradiation of copper K-α ray is recorded by the use of a recorder-equipped Geiger counter spectroscope to obtain diffraction patterns. Thus-obtained diffraction patterns are used to obtain the greatest intensity peak found in the lattice plane spacing d-value of 0.196±0.002 nm and the lattice plane spacing d-value of 0.386±0.008 nm from which the background is deducted to give the intensity ratio. The catalyst used in the invention is characterized by this intensity ratio. Use of the catalyst whose X-ray intensity ratio ranges from 7:100 to 35:100 is able to reduce the loss of xylene.

MFI-type zeolite and diluted alumina used as raw materials of the catalyst are preferably available in a powder form and must be molded when used as an industrial catalyst. Molding methods include compression molding, rolling molding, extrusion molding, and extrusion molding is preferable.

In the extrusion molding, inorganic binders such as alumina sol, alumina gel, bentonite and kaolina and surface active agents such as sodium dodecylbenzenesulfonate, sorbitan lauric acid monoester, sorbitan palmic acid monoester, sorbitan stearic acid monoester, sorbitan stearic acid triester, sorbitan oleic acid monoester, soribitan oleic acid trimester and their ethylene oxide additives (for example, Span or Twin made by ICI Inc.) are added, whenever necessary, as molding agents to MFI-type zeolite powder and alumina powder for attaining a uniform dispersion of the zeolite powder and then kneaded together. More preferable binders are alumina sol and alumina gel. Preferable rates in molding the catalyst are 15 to 80 weight parts for MFI-type zeolite, 20 to 85 weight parts for diluted alumina and 0 to 30 weight parts for inorganic binders in terms of the absolute dry standard (calculated on the basis of loss on ignition on 20-minute calcination at 500° C.). The more preferable rates are 20 to 60 weight parts for MFI-type zeolite, 40 to 80 weight parts for diluted alumina and 0 to 30 weight parts for inorganic binder. Where alumina is an inorganic binder such as alumina sol or alumina gel, MFI-type zeolite is at 15 to 80 weight parts, more preferably, at 20 to 80 weight parts. Where alumina ingredients are diluted alumina and an inorganic binder such as alumina sol or alumina gel, the zeolite is at 20 to 85 weight parts, or more preferably, at 60 to 80 weight parts on the basis of combined alumina ingredients. A kneaded ingredient is extruded from a screen. On an industrial scale, an extrusion machine called an extruder is used. The kneaded substance extruded from the screen is molded into a cylindrical form. A molded article is decided for the size by the diameter of the screen to be used. The diameter is preferably at 0.2 to 2.0 mmΦ, and more preferably at 0.5 to 1.7 mmΦ, providing cylindrical catalyst particles with the diameter of 0.2 to 2.0 mm. It is preferable that the cylindrical substance extruded from the screen should be treated with a machine called as "Marumerizer" for removing edges. Thus-molded article is a cylinder having 0.2 to 2.0 mm in diameter and 0.1 to 10 mm in length and dried at temperatures from 50° C. to 250° C. After drying, it is subjected to calcination at temperatures from 250° C. to 650° C., or preferably, from 350° C. to 600° C. for improving the molding strength. It is preferable to make the diameter of catalyst particles smaller than 2.0 mm and more preferable to make it smaller than 1.7 mm, because individual isomers of ethylbenzenes and xylenes are not delayed in diffusing to reaction activity points present inside the catalyst particles under reaction conditions or the reaction is not suppressed either. In particular, orthxylene and meta-xylene are not delayed in having isomerization reaction to para-xylene, and side reactions are not relatively augmented. In contrast, catalyst particles having the diameter greater than 0.2 mm would not render the pressure loss greater during the reaction, which is favorable.

These molded bodies are treated with the ion exchange to impart solid acidity. The methods for imparting solid acidity include a method to perform the ion exchange treatment with the compounds containing ammonium ion (for example, $NH_4Cl$, $NH_4NO_3$, $(NH_4)_2SO_4$) and introduce $NH_4$ ion into an ion exchange site of zeolite and then convert into hydrogen ion by drying and the calcination, and a method to introduce hydrogen ion into an ion exchange site of zeolite with the compounds containing acid (for example, HCl, $HNO_3$ and $H_3PO_4$).

Because the latter may damage the structure of zeolite, the former, that is to say, the compounds containing ammonium ion is preferably used for the ion exchange treatment. The latter may damage the structure of zeolite. It is also preferable that alkaline-earth metal ions should be available besides hydrogen ion in the invention. Alkaline-earth metals include magnesium, calcium, strontium and barium. Particularly preferable are calcium, strontium and barium because they can reduce the loss of xylene. MFI-type zeolite having the crystalline major axis and minor axis ranging from 0.03 to 0.7 micron and the silica/alumina mole ratio from 18 to 30 is particularly preferable because strontium and barium are able to greatly reduce the loss of xylene. The alkaline-earth metal ion exchange is treated with the compounds containing alkaline-earth metal ions (for example, chloride, nitrate and acetate) and introduces alkaline-earth metal ions into an ion exchange site of zeolite. Alkaline-earth metal ion exchange may be done at the same time with, before or after ammonium ion exchange. Further, preferably alkaline-earth metal can be introduced after adding the compounds containing alkaline-earth metal at the time of molding by kneading MFI-type zeolite powder with diluted alumina powder and binders. The content of alkaline-earth metals in relation to the catalyst (a total of MFI-type zeolite and inorganic oxide) is preferably at 0.05 to 5 weight % and more preferably at 0.1 to 2 weight %.

Introduction of silver ion is also preferable because of improvement in the catalyst activity.

Preferable content of silver ion is 0.1 to 5 weight %. Silver ion can be introduced by any method of ion exchange, impregnation or kneading, but the methods of the ion exchange are preferable. Silver ion exchange may be treated at the same time with alkaline-earth metal ion exchange or ammonium ion exchange, or may be treated separately. As a compound containing silver ion, silver nitrate is preferably used.

The hydrogenated active ingredients can be supported after such treatment. Hydrogen is allowed to be present in the catalyst reaction system to support the hydrogenated active ingredients, thereby making it possible to improve the hydrogenation and dealkylaton reaction activity of ethylbeneze into benzene and ethane as well as to control coking on the catalyst and prevent the deterioration with time of the property of the catalyst. As the hydrogenated active metal, rhenium, platinum and nickel are preferably used. Rhenium is particularly preferred. Rhenium can exist in such forms as metal, oxide, sulfide and selenium compound and the like. As the rhenium ingredients, perrhenic acid, perrhenic acid ammonium and others can be particularly preferred. As the platinum ingredients, chloroplatinic acid and chloroplatinic acid ammonium and others are particularly preferred. The quantity of the hydrogenated active ingredients to be supported is preferable from 0.005 to 1.5 weight % in relation to the catalyst in any case on metal conversion basis. An excessively smaller quantity of the hydrogenated active ingredients will result in an insufficient conversion activity of ethylbenzene while an excessively larger quantity of them will promote hydrogenation decomposition of alkyl aromatic hydrocarbons, both are not preferable.

After the hydrogenated active ingredients are supported, drying and the calcination are conducted. Ammonium ions present at an ion exchange point of MFI-type zeolite are converted into hydrogen ions, thus imparting acidity to the catalyst. Calcination can be preferably done at the temperature from 300° C. to 650° C. in an oxygen-containing atmosphere.

The catalyst of the invention is preferably treated by sulfuration after the hydrogenated active ingredients are supported. Usually, such treatment is done at the room temperature and up to 500° C., preferably at the temperature from 100° C. to 450° C. in a hydrogen sulfide atmosphere. The treatment by sulfuration is able to suppress the decomposition and the activity of alkyl aromatic hydrocarbons.

The method for converting xylenes including ethylbenzene described in the invention is to make the xylenes contact with the catalyst (the catalyst of the invention) under the presence of hydrogen. The conditions at the time of this contact is reaction temperatures from 300° C. to 480° C., preferably from 350° C. to 480° C., reaction pressure from 0.2 to 5 MPa, preferably from 0.4 to 3 MPa, $H_2$/C8 aromatic hydrocarbon mixtures (xylenes containing ethylbenzene) from 0.2 to 20 mol/mol, preferably from 1 to 10 mol/mol and weight space velocity from 0.2 to 30 $hr^{-1}$, preferably from 2 to 20 $hr^{-1}$.

Any C8 aromatic hydrocarbon mixtures may be used in the invention, as far as they contain ethylbenzene. Preferable mixtures are raw materials for producing p-xylene such as C8 aromatic hydrocarbon mixtures obtained by reforming naphtha and the subsequent extraction and/or fraction, C8 aromatic hydrocarbon mixtures obtained by reforming naphtha but not undergoing processes for extracting naphthene and paraffin to contain naphthene and paraffin having the carbon number of around 9, and C8 aromatic hydrocarbon mixtures obtained through extraction and/or fraction of cracked gasoline which is produced as a by-product of thermal decomposition of naphtha.

EMBODIMENTS

As follows, the present invention will be illustrated in more details referring to the embodiments. The invention is not limited to the following embodiments.

Embodiment 1 (Synthesis of MFI-type Zeolite and Preparation of Catalyst A)

Caustic soda aqueous solution (NaOH content of 48.6 weight %, $H_2O$ content of 51.4 weight %, Mitsuwaka Pure Chemical Co., Ltd.) of 40.9 g and tararic acid (Cahc Co., Ltd.) of 15.7 g were diluted with 529 g of water and dissolved. Soda aluminate solution ($Al_2O_3$ content of 18.9 weight %, NaOH of 25.4 weight %, $H_2O$ of 55.7 weight %, Daiso Co., Ltd.) of 12.83 g was added to thus-prepared solution to give a uniform solution. Hydrous silicate ($SiO_2$ content of 90.4 weight %, NaOH content of 0.22 weight %, $Al_2O_3$ content of 0.26 weight %, $H_2O$ content of 9.12 weight %, Nipseal VN-3, Japan Silica Corporation, now called Tosoh Silica Corporation) of 95.2 g was added gradually to the solution with stirring to prepare a uniform slurry of aqueous reaction mixture. The reaction mixture had the ingredient ratio (mole ratio) as follows.

| | |
|---|---|
| SiO$_2$/Al$_2$O$_3$ | 55 |
| OH/SiO$_2$ | 0.26 |
| A/Al$_2$O$_3$ | 40   (A: tartrate) |
| H$_2$O/SiO$_2$ | 22 |

The reaction mixture was placed in a 1000 ml-capacity autoclave and sealed, which was then made to react for 72 hours at 160° C., with stirring at 800 rpm. After completion of the reaction, thus-prepared mixture was repeatedly washed with distilled water and filtered 5 times, and then dried overnight at about 120° C.

The resultant substance was determined by an X-ray diffractiometer equipped with Cu tube and Kα-ray radiator, the result of which was shown in FIG. 1. It was found that the obtained zeolite was MFI-type zeolite.

Figure 2:
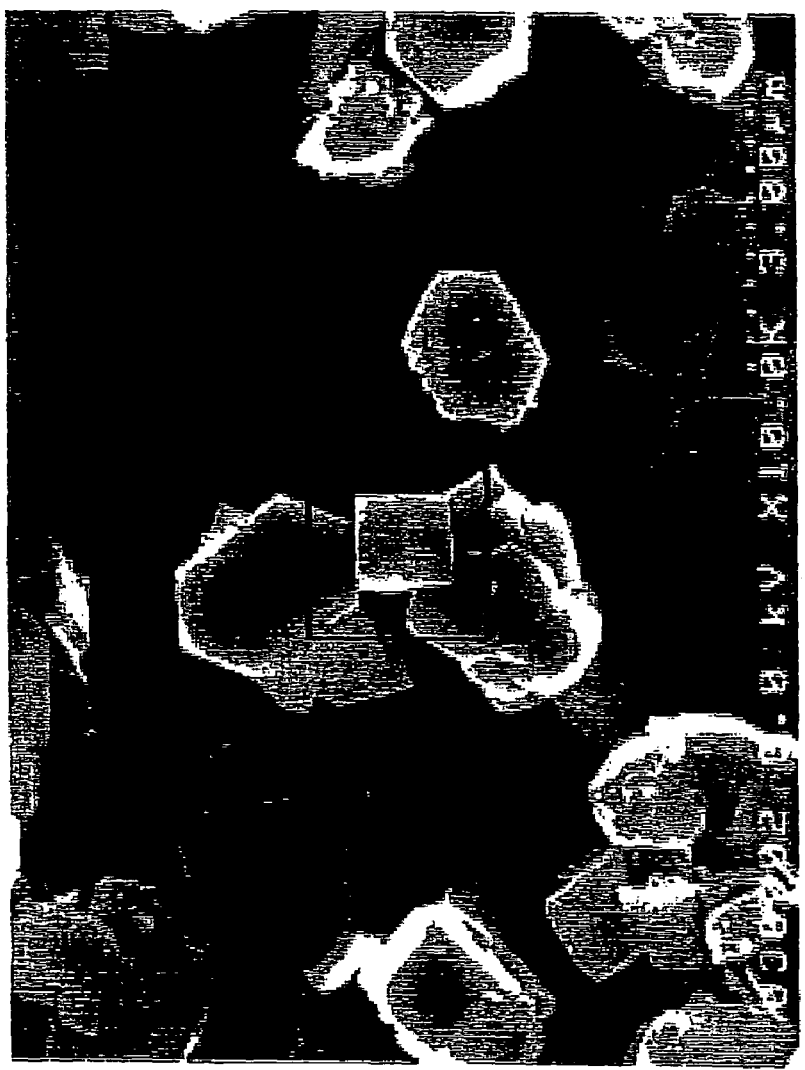
FIG. 2 is an FE-SEM observation view of MFI-type zeolite obtained in the embodiment 1 (of 10,000 powers)

The zeolite was subjected to FE-SEM observation, the result of which was shown in FIG. 2. The average size of the crystallite was of the major axis of 1.8 micron and the minor axis of 1.3 micron.

As the result of the analysis by a fluorescent X-ray diffraction, SiO$_2$/Al$_2$O$_3$ mole ratio of this zeolite was 43.

Figure 3:
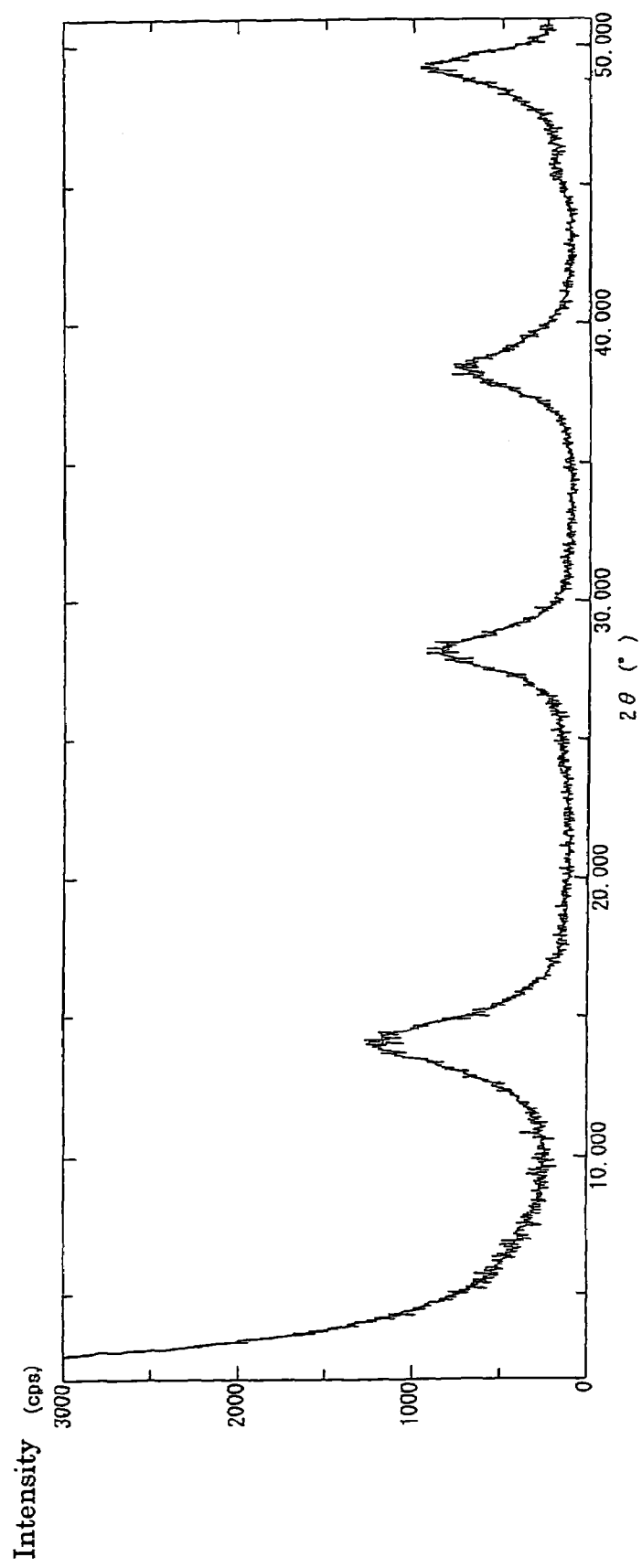
FIG. 3 is an X-ray diffraction pattern of hydrous alumina used in the embodiment 1.
Figure 4:
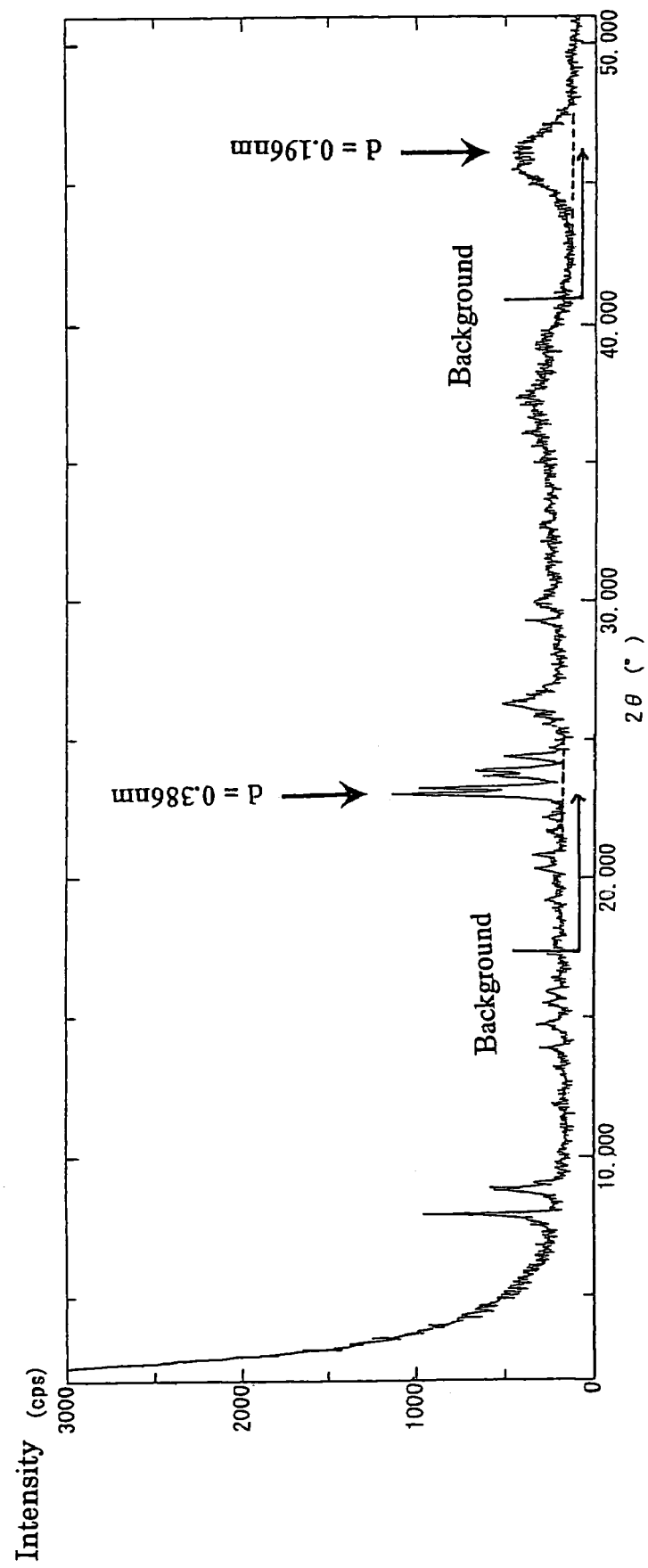
FIG. 4 is an X-ray diffraction pattern of the catalyst A obtained in the embodiment 1.

10 g of MFI-type zeolite synthesized as above mentioned on the basis of the absolute dry standard (calculated on the basis of loss on ignition at the time of the calcination for 20 minutes at 500° C.) was added to hydrous alumina (Al$_2$O$_3$ content of 75 weight %, the X-ray diffraction pattern shown in FIG. 3, SASOL Co., Ltd.) (30 g as Al$_2$O$_3$) of 40 g and alumina sol (Al$_2$O$_3$ content of 10 weight %, Nissan Chemical Industries Co., Ltd.) (6 g as Al$_2$O$_3$) of 60 g and well mixed. Thereafter, the resultant was placed in a dryer kept at 120° C. and dried until the moisture content was reduced to that of a clay. Thus-prepared kneaded substance was extruded through a screen having 1.2 mmΦ holes. The extruded mold body was dried overnight at 120° C. and calcined at 540° C. for 2 hours after raising the temperature gradually from 350° C. to 540° C. The calcined mold body of 20 g was placed in the aqueous solution in which ammonium chloride (Sigma Aldrich Corporation) of 2.2 g and calcium chloride dihydrate (Cahc Co., Ltd.) of 1.3 g were dissolved in 60 g of distilled water, and treated at 80° C. for 1 hour, with occasional stirring. After such treatment, the aqueous solution was removed and the resultant substance was repeatedly washed with distilled water and filtered 5 times. The substance was saturated with perrhenic acid aqueous solution (Rare Metal Production Co., Ltd.) of 30 ml containing Re of 80 mg at the room temperature and left stand for 2 hours. Stirring was conducted every 30 minutes. Then, the substance from which the moisture was removed was dried overnight at 120° C. After drying, the substance was treated with hydrogen sulfide at 250° C. for 2 hours in a hydrogen sulfide atmosphere, and then calcined at 540° C. for 2 hours in the air. As follows, the catalyst is abbreviated to "catalyst A". Calcium content and sodium content in the catalyst were determined by an atomic absorption spectroscopy, as a result, the content was 0.17 weight % as Ca and 0.3 weight % as Na. The quantity of rhenium supported in the catalyst was determined by an ICP emission spetrography, as a result, the quantity was 0.36 weight % as Re metal. This catalyst was ground and subjected to X-ray diffraction, the result of which was shown in FIG. 4. It was found in FIG. 4 that X-ray diffraction intensity ratio of the crystal lattice plane spacing d-value of 0.196 nm (2θ=46.18°) to the crystal lattice plane spacing d-value of 0.386 nm (2θ=23.04°) was 30:100.

2θ (°) value or d (nm) value in the X-ray diffraction pattern was obtained by referring to the Bragg's Law 2d×Sin θ=n×λ (on the conditions of n=1 and λ=0.15406 nm).

COMPARATIVE EXAMPLE 1

Preparation of Catalyst B

Figure 5:
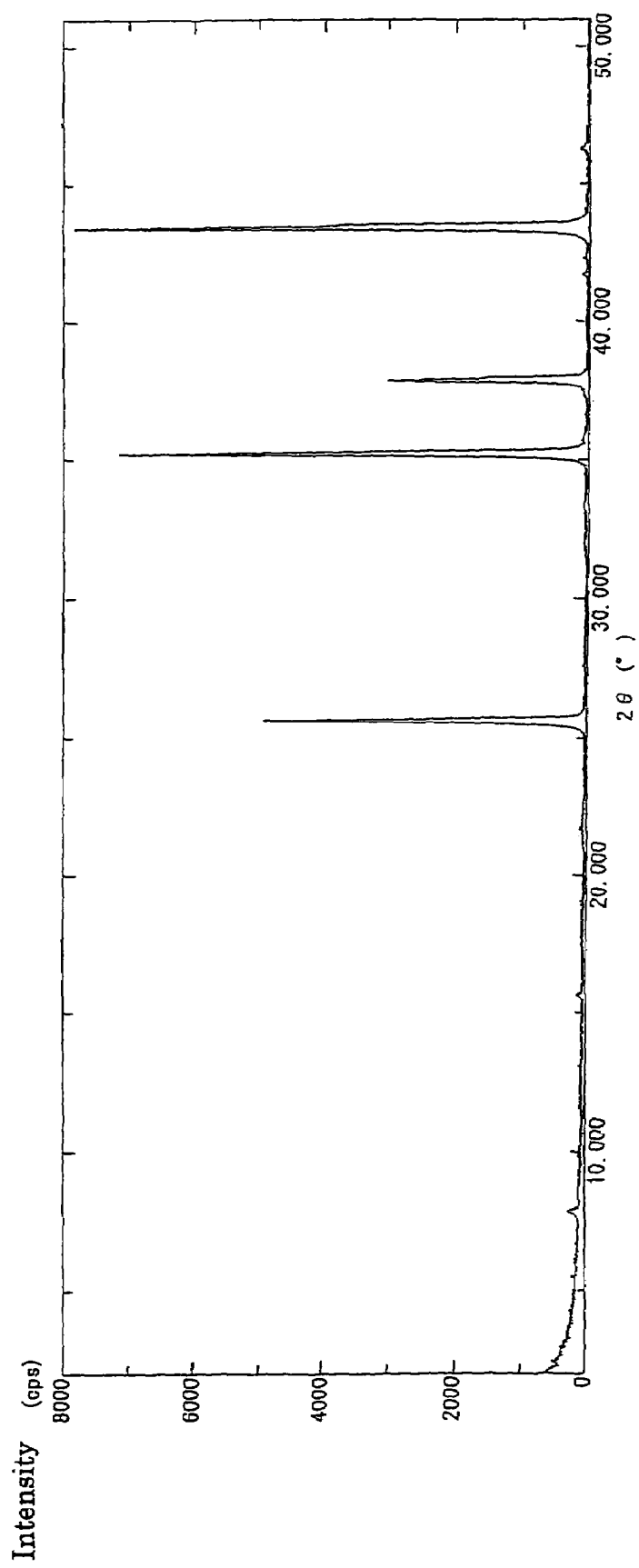
FIG. 5 is an X-ray diffraction pattern of the α-alumina used in the comparative example 1.
Figure 6:
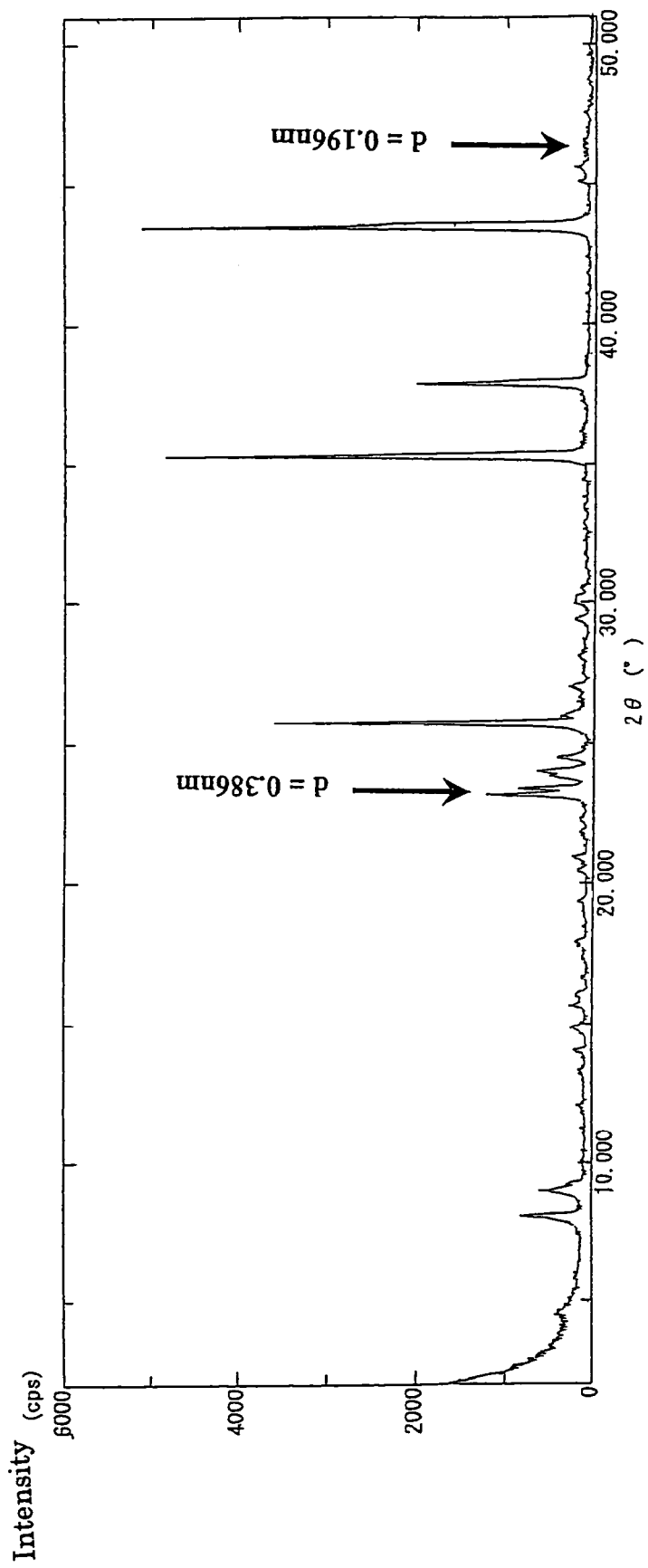
FIG. 6 is an X-ray diffraction pattern of the catalyst B obtained in the comparative example 1.

The MFI-type zeolite of 10 g synthesized similarly to in the embodiment 1 on the basis of the absolute dry standard (calculated on the basis of loss on ignition at the time of the calcination at 500° C. for minutes) was added to α-alumina (as Al$_2$O$_3$) (X-ray diffraction pattern shown in FIG. 5, Wako Pure Chemical Industries Co., Ltd.) of 30 g on the basis of the absolute dry standard and alumina sol (Al$_2$O$_3$ content of 10 weight %, Nissan Chemical Industries Co., Ltd.) (6 g as Al$_2$O$_3$) of 60 g and well mixed. Thereafter, the resultant was placed in a dryer kept at 120° C. and dried until the moisture content was reduced to that of a clay. Thus-prepared kneaded substance was extruded through a screen having 1.2 mmΦ holes. The extruded mold body was dried overnight at 120° C. and calcined at 540° C. for 2 hours after raising the temperature gradually from 350° C. to 540° C. The mold body of 20 g after the calcination was placed in the aqueous solution in which ammonium chloride (Sigma Aldrich Corporation) of 2.2 g and calcium chloride dihydrate (Cahc Co., Ltd.) of 1.3 g were dissolved in 60 g of distilled water, and treated at 80° C. for 1 hour, with occasional stirring. After such treatment, the aqueous solution was removed and the resultant substance was repeatedly washed with distilled water and filtered 5 times. The substance was immersed in perrhenic acid aqueous solution (Rare Metal Production Co., Ltd.) of 30 ml containing Re of 80 mg at the room temperature and left stand for 2 hours. Stirring was conducted every 30 minutes. Then, the substance from which the moisture was removed was dried overnight at 120° C. After drying, the substance was treated with hydrogen sulfide at 250° C. for 2 hours in the hydrogen sulfide atmosphere, and then calcined at 540° C. for 2 hours in the air. As follows, the catalyst is abbreviated to "catalyst B". Calcium content and sodium content in the catalyst were determined by the atomic absorption spectroscopy, as a result, the content was 0.18 weight % as Ca and 0.2 weight % as Na. The quantity of rhenium supported in the catalyst was determined by ICP emission spectrography, as a result, the quantity was 0.21 weight % as Re metal. This catalyst was ground and subjected to X-ray diffraction, the result of which was shown in FIG. 6. It was found in FIG. 6 that the crystal lattice plane spacing d-value of 0.386 nm (2θ=23.04°) was found whereas the crystal lattice plane spacing d-value of 0.196 nm (2θ=46.18°) was hardly found.

COMPARATIVE EXAMPLE 2

Preparation of Catalyst C

The MFI-type zeolite of 40 g synthesized similarly to in the embodiment 1 on the basis of the absolute dry standard (calculated on the basis of loss on ignition at the time of the calcinations at 500° C. for 20 minutes) was added to alumina sol (Al$_2$O$_3$ content of 10 weight %, Nissan Chemical Industries Ltd.) (6 g as Al$_2$O$_3$) of 60 g and well mixed.

Figure 7:
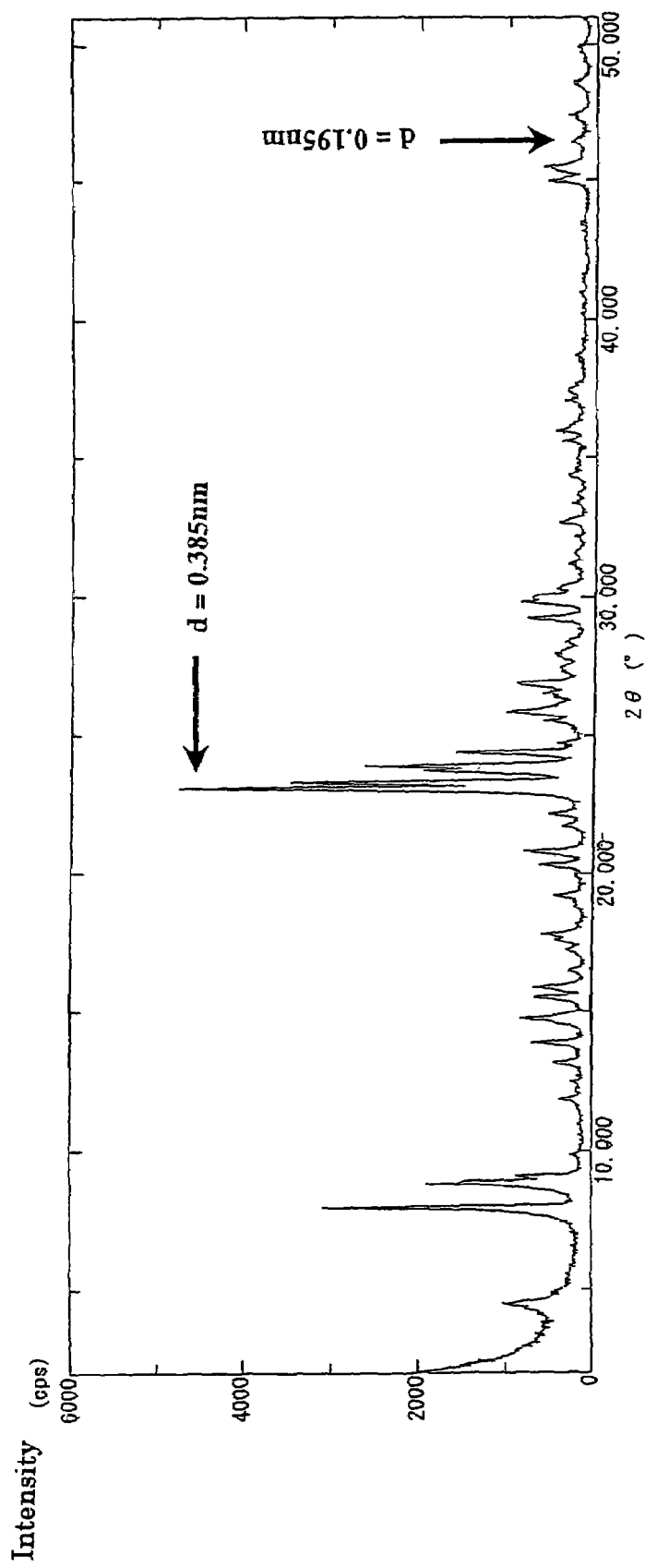
FIG. 7 is an X-ray diffraction pattern of the catalyst C obtained in the comparative example 2.

Thereafter, the resultant was placed in a dryer kept at 120° C. and dried until the moisture content was reduced to that of a clay. Thus-prepared kneaded substance was extruded through a screen having 1.2 mmΦ holes. The extruded mold body was dried overnight at 120° C. and calcined at 540° C.

for 2 hours after raising the temperature gradually from 350° C. to 540° C. The calcined mold body of 20 g was placed into an aqueous solution in which ammonium chloride (Sigma Aldrich Corporation) of 8.8 g and calcium chloride.dihydrate (Cahc Co., Ltd.) of 5.2 g were dissolved in distilled water of 60 g., and treated at 80° C. for 1 hour, with occasional stirring. After such treatment, the aqueous solution was removed and the resultant substance was repeatedly washed with distilled water and filtered 5 times. The substance was immersed in perrhenic acid aqueous solution (Rare Metal Production Co., Ltd.) of 30 ml containing 80 mg of Re at the room temperature and left stand for 2 hours. Stirring was conducted every 30 minutes. Then, the substance from which the moisture was removed was dried overnight at 120° C. After drying, the substance was treated with hydrogen sulfide at 250° C. for 2 hours in the hydrogen sulfide atmosphere, and then calcined at 540° C. for 2 hours in the air. As follows, the catalyst is abbreviated to "catalyst C". Calcium content and sodium content in the catalyst were determined by the atomic absorption spectroscopy, as a result, the content was 0.71 weight % as Ca and 0.5 weight % as Na. The quantity of rhenium supported in the catalyst was determined by the ICP emission spectrography, as a result, the quality was 0.21 weight % as Re metal. This catalyst was ground and subjected to X-ray diffraction, the result of which was shown in FIG. 7. It was found in FIG. 7 that the crystal lattice plane spacing d-value of 0.386 nm (2θ=23.04°) was found whereas the crystal lattice plane spacing d-value of 0.196 nm (2θ=46.18°) was not found or less than 100:5 at most, if any.

EMBODIMENT 2 (Preparation of Catalyst D)

The MFI-type zeolite of 20 g synthesized similarly to in the embodiment 1 on the basis of the absolute dry standard (calculated on the basis of loss on ignition at the time of the calcination at 500° C. for 20 minutes) was added to hydrous alumina ($Al_2O_3$ content of 75 weight %, the X-ray diffraction pattern shown in FIG. 3, SASOL Co., Ltd.) (20.2 g as $Al_2O_3$) of 27 g and alumina sol ($M_2O_3$ content of 10 weight %, Nissan Chemical Industries Ltd.) (6 g as $Al_2O_3$) of 60 g and well mixed. Thereafter, the resultant was placed in a dryer kept at 120° C. and dried until the moisture content was reduced to that of a clay. Thus-prepared kneaded substance was extruded through a screen having 1.2 mmΦ holes. The extruded mold body was dried overnight at 120° C. and calcined at 540° C. for 2 hours after raising the temperature gradually from 350° C. to 540° C. The calcined mold body of 20 g was placed into the aqueous solution in which ammonium chloride (Sigma Aldrich Corporation) of 2.8 g and calcium chloride dihydrate (Cahc Co., Ltd.) of 3.2 g were dissolved in distilled water of 60 g, and treated at 80° for 1 hour, with occasional stirring.

Figure 8:
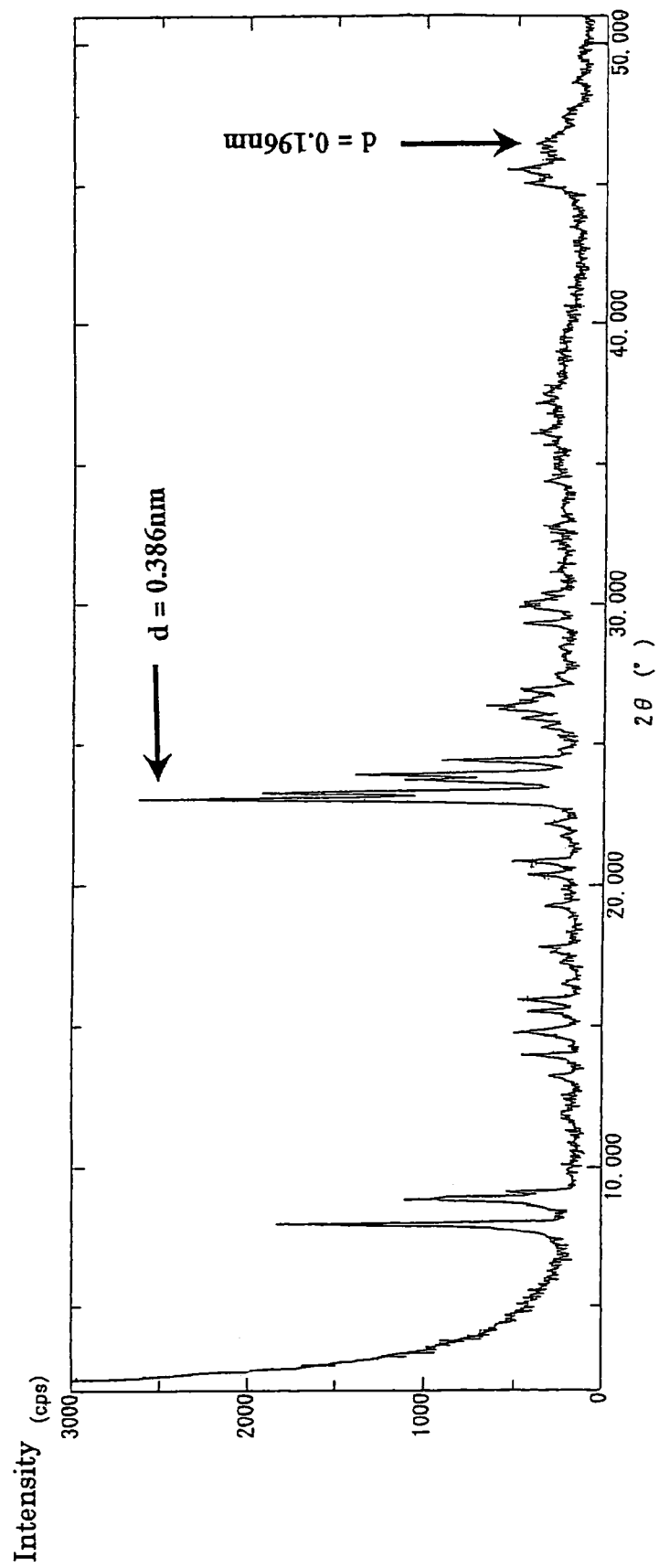
FIG. 8 is an X-ray diffraction pattern of the catalyst D obtained in the embodiment 2.

After such treatment, the aqueous solution was removed and the resultant substance was repeatedly washed with distilled water and filtered 5 times. The substance was immersed in perrhenic acid aqueous solution (Rare Metal Production Co., Ltd.) of 30 ml containing Re of 80 mg at the room temperature and left stand for 2 hours. Stirring was conducted every 30 minutes. Then, the substance from which the moisture was removed was dried overnight at 120° C. After drying, the substance was treated with hydrogen sulfide at 250° C. for 2 hours in the hydrogen sulfide atmosphere, and then calcined at 540° C. for 2 hours in the air. As follows, the catalyst is abbreviated to "catalyst D". Calcium content and sodium content of the catalyst were determined by the atomic absorption spectroscopy, as a result, the content was 0.43 weight % as Ca and 0.6 weight % as Na. The quantity of rhenium supported in the catalyst was determined by the ICP emission spectrography, as a result, the quality was 0.37 weight % as Re metal. This catalyst was ground and subjected to X-ray diffraction, the result of which was shown in FIG. 8. It was found in FIG. 8 that X-ray diffraction intensity ratio of the crystal lattice plane spacing d-value of 0.196 nm (2θ=46.18°) to the crystal lattice plane spacing d-value of 0.386 nm (2θ=23.04°) was 10:100.

The MFI-type zeolite of 10 g synthesized similarly to in the embodiment 1 on the basis of the absolute dry standard (calculated on the basis of loss on ignition at the time of the calcination at 500° C. for 20 minutes) was added to hydrous alumina ($Al_2O_3$ content of 75 weight %, the X-ray diffraction pattern shown in FIG. 3, SASOL Co., Ltd.) (30 g as $Al_2O_3$) of 40 g, alumina sol ($Al_2O_3$ content of 10 weight %, Nissan Chemical Industries Ltd.) (6 g as $Al_2O_3$) of 60 g and barium acetate (Cahc Co., Ltd.) of 1.5 g and well mixed. Thereafter, the resultant was placed in a dryer kept at 120° C. and dried until the moisture content was reduced to that of a clay. Thus-prepared kneaded substance was extruded through a screen having 1.2 mmΦ holes. The extruded mold body was dried overnight at 120° C. and calcined at 575° C. for 2 hours after raising the temperature gradually from 350° C. to 575° C. The calcined mold body of 20 g was placed into an aqueous solution in which ammonium chloride (Sigma Aldrich Corporation) of 1.1 g was dissolved in distilled water of 60 g, and treated at 80° C. for 1 hour, with occasional stirring. After such treatment, the aqueous solution was removed and the resultant substance was repeatedly washed with distilled water and filtered 5 times. The substance was immersed in perrhenic acid aqueous solution (Rare Metal Production Co., Ltd.) of 30 ml containing Re of 80 mg at the room temperature and left stand for 2 hours. Stirring was conducted every 30 minutes. Then, the substance from which the moisture was removed was dried overnight at 120° C. After drying, the substance was treated with hydrogen sulfide at 250° C. for 2 hours in the hydrogen sulfide atmosphere, and then calcined at 540° C. for 2 hours in the air.

As follows, the catalyst is abbreviated to "catalyst E". Barium content and sodium content in the catalyst were determined by the atomic absorption spectroscopy, as a result, the content was 0.39 weight % as Ba and 0.3 weight % as Na. The quantity of rhenium supported in the catalyst was determined by the ICP emission spectrography, as a result, the quantity was 0.37 weight % as Re metal. This catalyst was ground and subjected to X-ray diffraction, resulting in a finding that X-ray diffraction intensity ratio of the crystal lattice plane spacing d-value of 0.196 nm (2θ=46.18°) to the crystal lattice plane spacing d-value of 0.386 nm (2θ=23.04°) was 9:100.

The catalyst was prepared similarly to in the embodiment 1, chloroplatinic acid solution (Tanaka Rare Metal Co., Ltd.) in place of rhenium was immersed in the solution containing 100 weight ppm as Pt in relation to the catalyst. The Pt supported on the catalyst was determined by the ICP emission spectrography, as a result, it was 69 weight ppm. The catalyst is abbreviated to "catalyst F".

Embodiment 5 (Synthesis of MFI-type Zeolite and Preparation of Catalyst G)

Caustic soda aqueous solution (NaOH content of 48.6 weight %, $H_2O$ content of 51.4 weight %, Mitsuwaka Pure Chemical Co., Ltd.) of 37.1 g and 15.1 g of tararic acid (Cahc Co., Ltd.) were diluted with water of 529 g and dissolved. Soda aluminate solution ($Al_2O_3$ content of 18.9 weight %, NaOH of 25.4 weight %, $H_2O$ of 55.7 weight %, Daiso Co., Ltd.) of 14.25 g was added to thus-prepared solution to give a uniform solution. Hydrous silicate ($SiO_2$ content of 90.4 weight %, NaOH content of 0.22 weight %, $Al_2O_3$ content of 0.26 weight %, $H_2O$ content of 9.12 weight %, Nipseal VN-3, Japan Silica Corporation, now called Tosoh Silica Corporation) of 95.2 g was added gradually to the solution, with stirring, to prepare a uniform slurry of aqueous reaction mixture. The reaction mixture had the ingredient ratio (mole ratio) as follows.

| | | |
|---|---|---|
| $SiO_2/Al_2O_3$ | 50 | |
| $OH/SiO_2$ | 0.24 | |
| $A/Al_2O_3$ | 3.5 | (A: tartrate) |
| $H_2O/SiO_2$ | 22 | |

The reaction mixture was placed in a 1000 ml-capacity autoclave and sealed, which was then made to react at 160° C. for 72 hours with stirring at 800 rpm. After completion of the reaction, thus-prepared mixture was repeatedly washed with distilled water and filtered 5 times, and then dried overnight at about 120° C.

The resultant substance was determined by an X-ray diffractometer equipped with Cu tube and Kα-ray radiator, as a result, it was found that the obtained zeolite was MFI-type zeolite.

Figure 9:
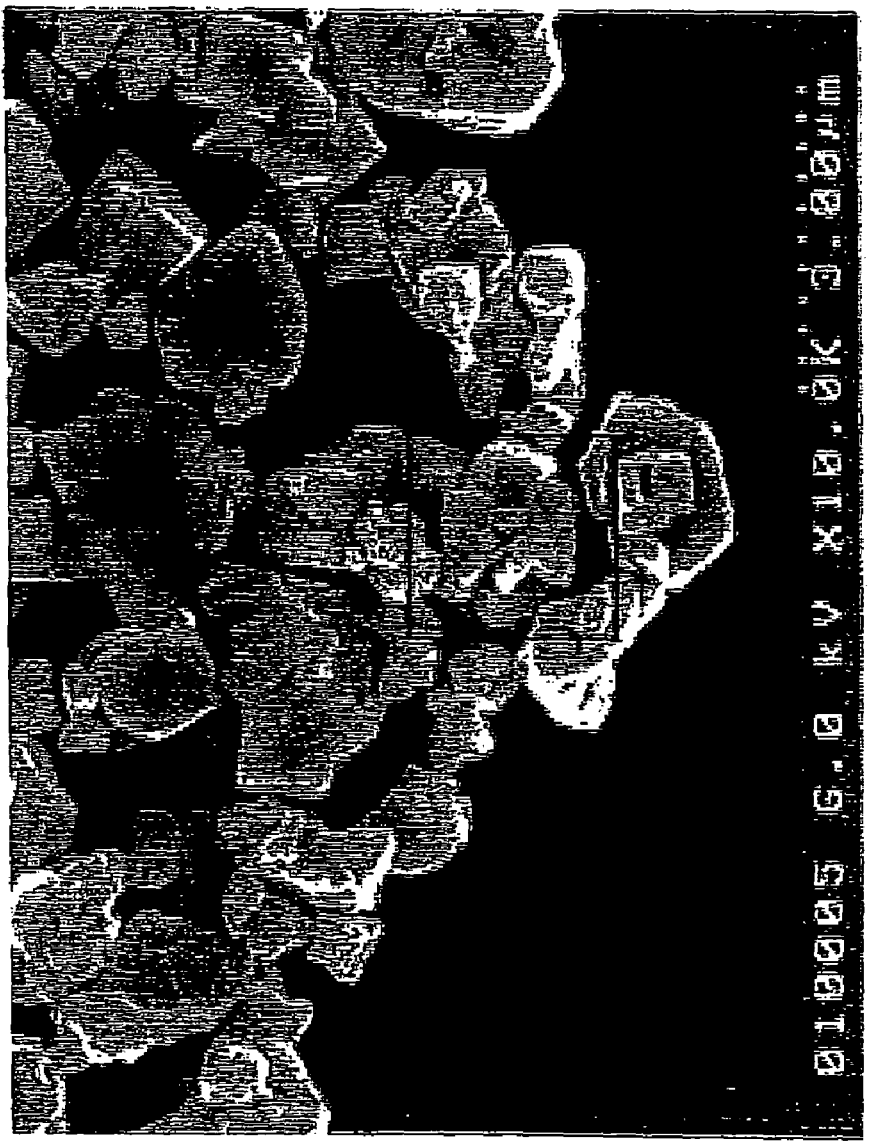
FIG. 9 is an FE-SEM observation view (magnified by 10,000 times) of MFI-type zeolite obtained in the embodiment 5.

The zeolite was subjected to FE-SEM observation, the result of which was shown in FIG. 9. The average size of the crystallite was of the major axis of 1.3 micron and the minor axis of 1.1 micron.

As a result of the analysis by the fluorescent X-ray diffraction, mole ratio $SiO_2/Al_2O_3$ of this zeolite was 37.

MFI-type zeolite of 10 g synthesized as above mentioned on the basis of the absolute dry standard (calculated on the basis of loss on ignition at the time of the calcination for 20 minutes at 500° C.) was added to hydrous alumina ($Al_2O_3$ content of 75% by weight, the X-ray diffraction pattern shown in FIG. 3, SASOL Co., Ltd.) (30 g as $Al_2O_3$) of 40 g and alumina sol ($Al_2O_3$ content of 10% by weight, Nissan Chemical Industries Co., LTd.) (6 g as $Al_2O_3$) of 60 g and well mixed. Thereafter, the resultant was placed in a dryer kept at 120° C. and dried until the moisture content was reduced to that of a clay. Thus-prepared kneaded substance was extruded through a screen having 1.2 mmΦ holes.

The extruded mold body was dried overnight at 120° C. and calcined at 540° C. for 2 hours after raising the temperature gradually from 350° C. to 540° C. 20 g of the calcined mold body was placed into an aqueous solution in which ammonium chloride (Sigma Aldrich Corporation) of 1.1 g and calcium chloride dihydrate (Cahc Co., Ltd.) of 1.3 g were dissolved in distilled water of 60 g., and treated at 80° C. for 1 hour, with occasional stirring. After such treatment, the aqueous solution was removed and the resultant substance was repeatedly washed with distilled water and filtered 5 times. The substance was immersed in perrhenic acid aqueous solution (Rare Metal Production Co., Ltd.) of 30 ml containing Re of 100 mg at the room temperature and left stand for 2 hours. Stirring was conducted every 30 minutes. Then, the substance from which the moisture was removed was dried overnight at 120° C. After drying, the substance was treated with hydrogen sulfide at 250° C. for 2 hours in the hydrogen sulfide atmosphere, and then calcined at 540° C. for 2 hours in the air. As follows, the catalyst is abbreviated to "catalyst G". Calcium content and sodium content in the catalyst were determined by the atomic absorption spectroscopy, as a result, the content was 0.18 weight % as Ca and 0.3 weight % as Na. The quantity of rhenium supported in the catalyst was determined by the ICP emission spectrography, as a result, the quantity was 0.47 weight % as Re metal. This catalyst was ground and subjected to X-ray diffraction, resulting in a finding that X-ray diffraction intensity ratio of the crystal lattice plane spacing d-value of 0.196 nm (2θ=46.18°) to the crystal lattice plane spacing d-value of 0.386 nm (2θ=23.04°) was 9:100.

The MFI-type zeolite of 15 g synthesized similarly to in the embodiment 5 on the basis of the absolute dry standard (calculated on the basis of loss on ignition at the time of the calcination at 500° C. for 20 minutes) was added to hydrous alumina ($Al_2O_3$ content of 75 weight %, the X-ray diffraction pattern shown in FIG. 3, SASOL Co., Ltd.) (25.5 g as $Al_2O_3$) of 34 g alumina sol ($Al_2O_3$ content of 10 weight %, Nissan Chemical Industries Ltd.) (6 g as $Al_2O_3$) of 60 g and calcium chloride dihydrate of 3.0 g and well mixed. Thereafter, the resultant was placed in a dryer kept at 120° C. and dried until the moisture content was reduced to that of a clay. Thus-prepared kneaded substance was extruded through a screen having 1.2 mmΦ holes. The extruded mold body was dried overnight at 120° C. and calcined at 540° C. for 2 hours after raising the temperature gradually from 350° C. to 540° C. The calcined mold body of 20 g was placed into an aqueous solution in which ammonium chloride (Sigma Aldrich Corporation) of 1.6 g was dissolved in distilled water of 60 g, and treated at 80° C. for 1 hour, with occasional stirring. After such treatment, the aqueous solution was removed and the resultant substance was repeatedly washed with distilled water and filtered 5 times. The substance was immersed in perrhenic acid aqueous solution (Rare Metal Production Co., Ltd.) of 30 ml containing Re of 80 mg at the room temperature and left stand for 2 hours. Stirring was conducted every 30 minutes. Then, the substance from which the moisture was removed was dried overnight at 120° C. After drying, the substance was treated with hydrogen sulfide at 250° C. for 2 hours in the hydrogen sulfide atmosphere, and then calcined at 540° C. for 2 hours in the air. As follows, the catalyst is abbreviated to "catalyst H". Calcium content and sodium content of the catalyst were determined by the atomic absorption spectroscopy, as a result, the content was 0.37 weight % as Ca and 0.2 weight % as Na. The quantity of rhenium supported in the catalyst was determined by the ICP emission spectrography, as a result, the quantity was 0.38 weight % as Re metal. This catalyst was ground and subjected to X-ray diffraction, resulting in a finding that X-ray diffraction intensity ratio of the crystal lattice plane spacing d-value of 0.196 nm (2θ=46.18°) to the crystal lattice plane spacing d-value of 0.386 nm (2θ=23.04°) was 10:100.

The catalyst prepared similarly as in the embodiment 5 was placed into a solution in which nickel nitrate solution (Hayashi Pure Chemical Industries Ltd.) was contained in place of rhenium at 1000 weight ppm as Ni in relation to the catalyst. The Ni supported on the catalyst was determined by the ICP emission spectrography, as a result, the quantity was 850 weight ppm. The catalyst is abbreviated to "catalyst I"

Embodiment 8 (Preparation of Catalyst J)

Raw materials similar to those used in the embodiment 1 were used to prepare an aqueous reaction mixture having the following ingredients.

| | | |
|---|---|---|
| SiO$_2$/Al$_2$O$_3$ | 77 | |
| OH—/SiO$_2$ | 0.30 | |
| A/Al$_2$O$_3$ | 5.0 | (A: tartrate) |
| H$_2$O/SiO$_2$ | 25 | |

The reaction mixture was put in an autoclave capacity of 1000 mL to be sealed, which was then allowed to react for 72 hours at 160° C., while being stirred at 800 rpm. After the reaction was over, the mixture was washed with distilled water and filtered repeatedly 5 times, and then dried at about 120° C. overnight.

The resultant substance was determined by an X-ray diffractometer equipped with Cu tube and K alpha ray radiator. The substance was found to be MFI-type zeolite.

Figure 10:
FIG. 10 is an FE-SEM observation view (of 10,000 powers) of MFI-type zeolite obtained in the embodiment 8.

The result of FE-SEM observation of zeolite is shown in FIG. 10. The average crystallite size was 1.5 micron at the major axis and 1.5 micron at the minor axis.

The SiO$_2$/Al$_2$O$_3$ mole ratio of the zeolite was found to be 51 by a fluorescent X-ray diffraction analysis.

Hydrous alumina (Al$_2$O$_3$ content of 75 weight %, X-ray diffraction pattern shown in FIG. 3, SASOL Ltd.) of 40 g. (equivalent to Al$_2$O$_3$ of 30 g.) and alumina sol (Al$_2$O$_3$ content of 10 weight %, Nissan Chemical Industries Ltd.) of 60 g. (equivalent to Al$_2$O$_3$ of 6 g.) were added to above-synthesized MFI-type zeolite of 10 g. on the basis of the absolute dry standard (calculated from the loss on ignition during 20-minute calcination at 500° C.) to be well mixed. Thereafter, the resultant mixture was placed in a dryer kept at 120° C. and dried until the moisture content was reduced to that of a clay. The kneaded mixture was extruded through a screen having 1.2 mmΦ holes. The extruded mold body was dried at 120° C. overnight and put under calcination at 540° C. for 2 hours after gradual elevation of temperatures from 350° C. to 540° C. The calcinated mold body of 20 g. was added in an aqueous solution in which ammonium chloride (Sigma Aldrich Corporation) of 1.1 g. and calcium chloride dihydrate (Cahc Co., Ltd.) of 1.3 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. Furthermore the mixture was immersed in a perrhenic acid aqueous solution (Rare Metal Production Co., Ltd.) of 30 mL containing Re of 100 mg and left at room temperature for 2 hours, while being stirred every 30 minutes. After the moisture in the mixture was removed and the mixture was dried at 120° C. Overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst J" hereinafter. Contents of calcium and sodium in the catalyst were determined by an atomic absorption spectrometry, resulting that Ca and Na were of 0.15 weight % and 0.3 weight % respectively. A quantity of rhenium supported in the catalyst was determined by ICP emission spectroscopy, resulting Re metal to be of 0.37 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 11:100.

Raw materials similar to those used in the embodiment 1 were used to prepare an aqueous reaction mixture having the following ingredients.

| | | |
|---|---|---|
| SiO$_2$/Al$_2$O$_3$ | 30 | |
| OH—/SiO$_2$ | 0.175 | |
| A/Al$_2$O$_3$ | 2.5 | (A: tartrate) |
| H$_2$O/SiO$_2$ | 20 | |

The reaction mixture was put in an autoclave capacity of 1000 mL to be sealed, which was then allowed to react for 72 hours at 160° C., while being stirred at 800 rpm. After the reaction was over, the mixture was washed with distilled water and filtered repeatedly 5 times, and then dried at about 120° C. overnight.

The resultant substance was determined by an X-ray diffractometer equipped with Cu tube and K alpha ray radiator. The substance was found to be MFI-type zeolite.

Figure 11:
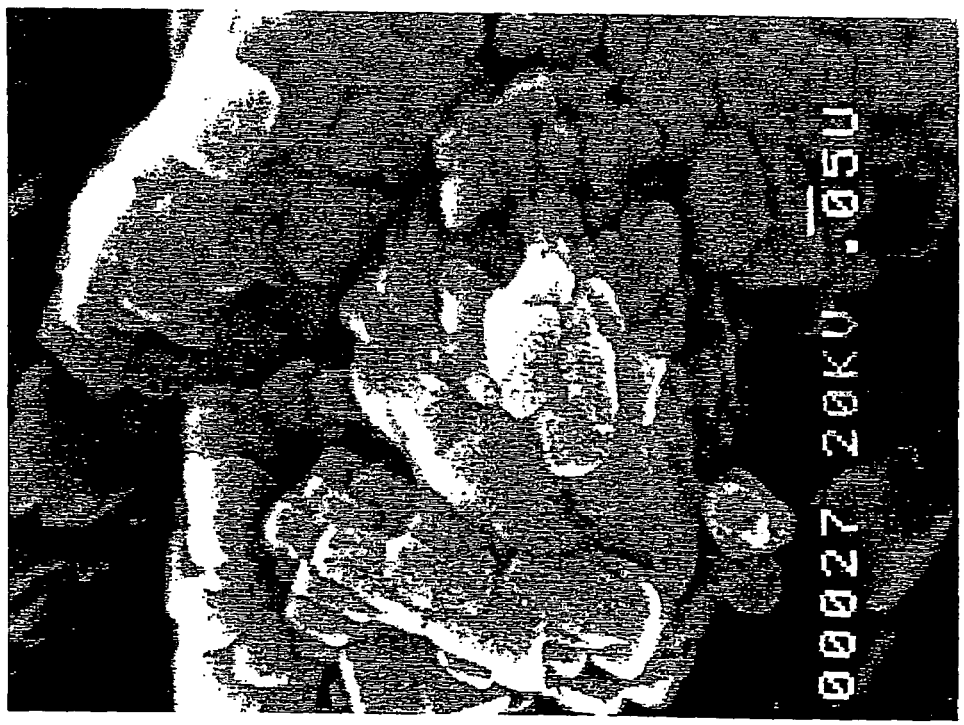
FIG. 11 is an FE-SEM observation view (magnified by 100,000 times) of MFI-type zeolite obtained in the embodiment 9.

The result of FE-SEM observation of zeolite is shown in FIG. 11. The average crystallite size was 0.05 micron at the major axis and 0.05 micron at the minor axis.

The SiO$_2$/Al$_2$O$_3$ mole ratio of the zeolite was found to be 25 by a fluorescent X-ray diffraction analysis.

The above-synthesized MFI-type zeolite powder of 30 g. on the basis of the absolute dry standard (calculated from the loss on ignition during 20-minute calcination at 500° C.) was added to an aqueous solution in which ammonium chloride (Sigma Aldrich Corporation) of 15.2 g. was dissolved in distilled water of 150 g. and treated at 80° C. for 1 hour while being stirred intermittently. After such treatment, the aqueous solution was removed and the resultant mixture was washed with distilled water and filtered repeatedly 5 times. The resultant mixture was immersed in a perrhenic acid aqueous solution (Rare Metal Production Co., Ltd.) of 100 mL containing Re of 150 mg at room temperature and left for 2 hours, while being stirred every 30 minutes. After the moisture in the mixture was removed and the mixture was dried at 120° C. overnight, the resultant mixture was molded into a 3 mm-across cylinderical form by a tablet machine. The mold body of 25 g. was ground to be classified by crashing to obtain a mold body of 15 g. having 12 to 24 meshes. The mold body was treated with hydrogen sulfide at 250° C. for 2 hours in a hydrogen sulfide stream and put under calcination at 540° C. for 2 hours in the atmosphere. This catalyst is referred to as "catalyst K" hereinafter. Sodium content in the catalyst was determined by the atomic absorption spectrometry, resulting Na to be of 0.4 weight %. A quantity of rhenium supported in the catalyst was determined by ICP emission spectroscopy, resulting Re metal to be of 0.11 weight %. This catalyst was ground to be measured by X-ray diffraction. FIG. 12 shows the result and the X-ray diffraction intensity ratio of the crystal lattice spacing d-value of 0.196 nm (2θ=46.18°) to the crystal lattice spacing d-value of 0.386 nm (2θ=23.04°) was proved to be 3:100.

Catalysts from A to K were filled into reaction tubes respectively by 7.5 g. and xylenes containing ethylbenzene were put under gas phase reaction in the presence of hydrogen. Table 1 and Table 2 show the results.

TABLE 1

Performance of each catalyst

| | Supplied raw material | Embodiment 10 | Embodiment 11 | Embodiment 12 | Embodiment 13 | Embodiment 14 | Embodiment 15 | Embodiment 16 | Embodiment 17 |
|---|---|---|---|---|---|---|---|---|---|
| Reaction condition | | Catalyst A | Catalyst D | Catalyst E | Catalyst F | Catalyst G | Catalyst H | Catalyst I | Catalyst J |
| Reaction temperature ° C. | | 360 | 365 | 391 | 360 | 368 | 370 | 363 | 375 |
| Reaction pressure MPa-G | | 0.64 | 0.64 | 0.64 | 0.64 | 0.64 | 0.64 | 0.64 | 0.64 |
| W/F g-cat · hr/g-mol | | 30 | 15 | 30 | 30 | 30 | 30 | 30 | 30 |
| H2/F mol/mol | | 3.5 | 3.5 | 3.5 | 3.5 | 3.5 | 3.5 | 3.5 | 3.5 |
| C1 wt % | | 0.00 | 0.00 | 0.00 | 0.05 | 0.00 | 0.01 | 0.01 | 0.00 |
| C2 | | 2.67 | 2.39 | 3.04 | 2.44 | 2.64 | 2.99 | 2.33 | 2.41 |
| C3 | | 0.06 | 0.08 | 0.04 | 0.11 | 0.05 | 0.06 | 0.13 | 0.08 |
| C4 | | 0.01 | 0.01 | 0.01 | 0.10 | 0.01 | 0.01 | 0.08 | 0.01 |
| C7- wt % | 0.00 | 0.05 | 0.05 | 0.06 | 0.12 | 0.06 | 0.06 | 0.09 | 0.08 |
| C8NP | 0.07 | 0.04 | 0.05 | 0.06 | 0.15 | 0.08 | 0.06 | 0.12 | 0.09 |
| BZ | 0.01 | 6.95 | 6.36 | 7.67 | 6.09 | 6.71 | 7.62 | 5.90 | 7.18 |
| TOL | 1.50 | 2.35 | 2.41 | 2.47 | 3.01 | 2.17 | 2.55 | 2.15 | 2.41 |
| EB | 15.16 | 4.75 | 5.24 | 3.58 | 5.40 | 5.06 | 3.57 | 6.08 | 4.98 |
| p-X | 0.91 | 19.21 | 19.02 | 18.65 | 18.94 | 19.14 | 19.27 | 18.97 | 19.13 |
| m-X | 56.80 | 43.41 | 43.43 | 43.35 | 43.17 | 43.39 | 43.32 | 43.15 | 43.22 |
| o-X | 25.47 | 19.87 | 20.07 | 20.52 | 19.91 | 20.09 | 19.85 | 19.90 | 19.64 |
| Pr-B | 0.00 | 0.00 | 0.00 | 0.00 | 0.00 | 0.00 | 0.00 | 0.00 | 0.00 |
| ET | 0.03 | 0.14 | 0.23 | 0.14 | 0.11 | 0.16 | 0.14 | 0.25 | 0.20 |
| TMB | 0.03 | 0.23 | 0.24 | 0.23 | 0.25 | 0.23 | 0.31 | 0.23 | 0.24 |
| DEB | 0.00 | 0.14 | 0.27 | 0.13 | 0.07 | 0.15 | 0.10 | 0.41 | 0.20 |
| EX | 0.00 | 0.12 | 0.15 | 0.05 | 0.08 | 0.06 | 0.07 | 0.20 | 0.14 |
| C10+ | 0.00 | 0.00 | 0.01 | 0.01 | 0.00 | 0.00 | 0.00 | 0.00 | 0.00 |
| EB conversion wt % | | 68.6 | 65.4 | 76.4 | 64.4 | 66.6 | 76.5 | 59.9 | 67.2 |
| p-X/ΣX | | 23.3 | 23.1 | 22.6 | 23.1 | 23.2 | 23.4 | 23.0 | 23.3 |
| XY loss | | 0.8 | 0.8 | 0.8 | 1.4 | 0.7 | 0.9 | 1.4 | 1.4 |

C1: Methane,
C2: Methane, Ethylene,
C3: Aliphatic hydrocarbon of carbon number of 3,
C4: Aliphatic hydrocarbon of carbon number of 4,
C7-: Aliphatic hydrocarbon of carbon number of 5 to 7,
C8NP: Aliphatic hydrocarbon of carbon number of 8,
BZ: Benzene,
TOL: Toluene,
EB: Ethylbenzene,
p-X Para-xylene,
m-X Meta-xylene,
o-X Ortho-xylene,
Pr-B Propyl benzene,
ET: Ethyl toluen,
TMB: Trimethyl benzene,
DEB: Diethylbenzene,
EX: Ethyl xylene,
C10+: Tetramethylbenzene and aromatic hydrocarbon of carbon number of 11 or more,
EB conversion: Rate of converted ethylbenzene in raw materials supplied due to reaction,
p-X/ΣX: Concentration of para-xylene in isomer mixtures,
XY loss: Rate of xylene lost due to reaction

TABLE 2

Performance of each catalyst

| | Supplied raw material | Embodiment 4 | Embodiment 5 | Embodiment 6 |
|---|---|---|---|---|
| Reaction condition | | Catalyst B | Catalyst C | Catalyst K |
| Reaction temperature ° C. | | 360 | 360 | 360 |
| Reaction pressure MPa-G | | 0.64 | 0.64 | 0.64 |
| W/F g-cat.hr/g-mol | | 30 | 30 | 30 |
| H2/F mol/mol | | 3.5 | 3.5 | 3.5 |
| C1 wt % | | 0.00 | 0.00 | 0.00 |
| C2 | | 2.47 | 3.24 | 3.21 |
| C3 | | 0.04 | 0.10 | 0.08 |
| C4 | | 0.01 | 0.02 | 0.03 |
| C7-wt % | 0.00 | 0.03 | 0.05 | 0.04 |
| C8NP | 0.07 | 0.03 | 0.06 | 0.03 |
| BZ | 0.01 | 5.37 | 6.37 | 5.11 |
| TOL | 1.50 | 2.00 | 3.22 | 5.69 |

TABLE 2-continued

Performance of each catalyst

| | Supplied raw material | Embodiment 4 | Embodiment 5 | Embodiment 6 |
|---|---|---|---|---|
| EB | 15.16 | 6.26 | 4.17 | 5.17 |
| p-X | 0.91 | 18.59 | 18.84 | 17.78 |
| m-X | 56.80 | 42.53 | 42.31 | 39.34 |
| o-X | 25.47 | 19.73 | 19.37 | 17.91 |
| Pr-B | 0.00 | 0.00 | 0.00 | 0.00 |
| ET | 0.03 | 0.44 | 0.33 | 1.21 |
| TMB | 0.03 | 0.43 | 0.32 | 2.95 |
| DEB | 0.00 | 1.07 | 0.85 | 0.62 |
| EX | 0.00 | 0.96 | 0.72 | 0.65 |
| C10+ | 0.00 | 0.04 | 0.03 | 0.18 |
| EB conversion wt % | | 58.7 | 72.5 | 65.9 |
| p-X/ΣX | | 23.0 | 23.4 | 23.7 |
| XY loss | | 2.8 | 3.2 | 9.8 |

According to the comparison of the embodiments from 10 to 17 with the comparative examples from 4 to 6, the conversion catalyst for xylenes containing ethylbenzene in which X-ray diffraction intensity ratio of the crystal lattice spacing d-value of 0.196 nm±0.002 nm to the crystal lattice spacing d-value of 0.386 nm±0.008 nm ranges from 7:100 to 35:100 shows low xylene loss under reaction conditions where the ethylbenzene conversion rate and the rate of isomerization to para-xylene are high.

Hydrous alumina ($Al_2O_3$ content of 75 weight %, SASOL Ltd.) of 40 g. (equivalent to $Al_2O_3$ of 30 g.) and alumina sol ($Al_2O_3$ content of 10 weight %, Nissan Chemical Industries Ltd.) of 60 g. (equivalent to $Al_2O_3$ of 6 g.) were added to the MFI-type zeolite synthesized similarly as in the embodiment 1 on the basis of the absolute dry standard (calculated from the loss on ignition during 20-minute calcination at 500° C.) of 10 g. to be well mixed. Thereafter, the resultant mixture was placed in a dryer kept at 120° C. and dried until the moisture content was reduced to that of a clay. The kneaded mixture was extruded through a screen having 1.2 mmΦ holes. The extruded mold body was dried at 120° C. overnight and put under calcination at 540° C. for 2 hours after gradual elevation of temperatures from 350° C. to 540° C. The calcinated mold body of 20 g. was added to an aqueous solution in which ammonium chloride (Sigma Aldrich Corporation) of 2.2 g. was dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in a perrhenic acid aqueous solution (Rare Metal Production Co., Ltd.) of 30 mL containing Re of 80 mg at room temperature and left for 2 hours, while being stirred every 30 minutes. After the moisture in the mixture was removed and the mixture was dried at 120° C. overnight, the resultant mixture was treated with hydrogen sulfide at 250° C. for 2 hours in a hydrogen sulfide stream, and subsequently put under calcination at 540° C. for 2 hours in the atmosphere. This catalyst is referred to as "catalyst L" hereinafter. Sodium content in the catalyst was determined by the atomic absorption spectrometry, resulting Na to be of 0.4 weight %. A quantity of rhenium supported in the catalyst was determined by ICP emission spectroscopy, resulting Re metal to be of 0.35 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 31:100.

Hydrous alumina ($Al_2O_3$ content of 75 weight %, SASOL Ltd.) of 40 g. (equivalent to $Al_2O_3$ of 30 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 10 g. synthesized similarly as in the embodiment 1 on the basis of the absolute dry standard (calculated from the loss on ignition during 20-minute calcination at 500° C.) to be well mixed. Thereafter, the resultant mixture was placed in a dryer kept at 120° C. and dried until the moisture content was reduced to that of a clay. The kneaded mixture was extruded through a screen having 1.2 mmΦ holes. The extruded mold body was dried at 120° C. overnight and put under calcination at 540° C. for 2 hours after gradual elevation of temperatures from 350° C. to 540° C. The calcinated mold body of 20 g. was added to an aqueous solution in which ammonium chloride (Sigma Aldrich Corporation) of 2.2 g. and magnesium chloride hexahydrate (Cahc Co. Ltd.) of 1.8 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in an aqueous perrhenic acid solution (Rare Metal Production Co., Ltd.) of 30 mL containing Re of 80 mg at room temperature and left for 2 hours, while being stirred every 30 minutes. After the moisture in the mixture was removed and the mixture was dried at 120° C. overnight, the mixture was treated with hydrogen sulfide at 250° C. for 2 hours in a hydrogen sulfide stream, subsequently put under calcination at 540° C. for 2 hours in the atmosphere. This catalyst is referred to as "catalyst M" hereinafter. Contents of magnesium and sodium in the catalyst were determined by the atomic absorption spectrometry, resulting that Mg and Na were of 0.13 weight % and 0.3 weight % respectively. A quantity of rhenium supported in the catalyst was determined by ICP emission spectroscopy, resulting Re metal to be of 0.35 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 30:100.

Hydrous alumina ($Al_2O_3$ content of 75 weight %, SASOL Ltd.) of 40 g. (equivalent to $Al_2O_3$ of 30 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 10 g. synthesized similarly as in the embodiment 1 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 1.2 mmΦ holes. The extruded mold body was dried at 120° C. overnight and put under calcination at 540° C. for 2 hours after gradual elevation of temperatures from 350° C. to 540° C. The calcinated mold body of 20 g. was added in an aqueous solution in which ammonium chloride (Sigma Aldrich Corporation) of 1.1 g. and calcium chloride dihydrate (Cahc Co., Ltd.) of 1.8 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in an aqueous perrhenic acid solution (Rare Metal Production Co., Ltd.) of 30 mL containing Re of 80 mg at room temperature and left for 2 hours, while being stirred every 30 minutes. After the moisture in the mixture was removed and the mixture was dried at 120° C. overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst N" hereinafter. Contents of calcium and sodium in the catalyst were determined by the atomic absorption spectrometry, resulting that Ca and Na were of 0.18 weight % and 0.3 weight % respectively. A quantity of rhenium supported in the catalyst was determined by ICP emission spectroscopy, resulting Re metal to be of 0.35 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 30:100.

Hydrous alumina ($Al_2O_3$ content of 75 weight %, SASOL Ltd.) of 40 g. (equivalent to $Al_2O_3$ of 30 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 10 g. synthesized similarly as in the embodiment 1 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 1.2 mmΦ holes. The extruded mold body was dried at 120° C. overnight and put under calcination at 540° C. for 2 hours after gradual elevation of temperatures from 350° C. to 540%. The calcinated mold body of 20 g. was added to an aqueous solution in which ammonium chloride (Sigma Aldrich Corporation) of 1.1 g. and strontium nitrate (Cahc Co., Ltd.) of 1.9 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in an aqueous perrhenic acid solution (Rare Metal Production Co., Ltd.) of 30 mL containing Re of 80 mg at room temperature and left for 2 hours, while being stirred every 30 minutes. After the moisture of the mixture was removed and the mixture was dried at 120° C. overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst O" hereinafter. Contents of strontium and sodium in the catalyst were determined by the atomic absorption spectrometry, resulting that Sr and Na were of 0.20 weight % and 0.3 weight % respectively. A quantity of rhenium supported in the catalyst was determined by ICP emission spectroscopy, resulting Re metal to be of 0.35 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 30:100.

Hydrous alumina ($Al_2O_3$ content of 75 weight %, SASOL Ltd.) of 33.3 g. (equivalent to $Al_2O_3$ of 25 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 15 g. synthesized similarly as in the embodiment 1 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 0.5 mmΦ holes. The extruded mold body was dried at 120° C. overnight and put under calcination at 540° C. for 2 hours after gradual elevation of temperatures from 350° C. to 540° C. The calcinated mold body of 20 g. was added to an aqueous solution in which ammonium chloride (Sigma Aldrich Corporation) of 1.65 g. and calcium chloride dihydrate (Cahc Co., Ltd.) of 2.7 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in an aqueous perrhenic acid solution (Rare Metal Production Co., Ltd.) of 30 mL containing Re of 80 mg at room temperature and left for 2 hours, while being stirred every 30 minutes. After the moisture in the mixture was removed and the mixture was dried at 120° C. overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst P" hereinafter. Contents of calcium and sodium in the catalyst were determined by the atomic absorption spectrometry, resulting that Na and Ca were of 0.27 weight % and 0.3 weight % respectively. A quantity of rhenium supported in the catalyst was determined by ICP emission spectroscopy analysis, resulting Re metal to be of 0.37 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 15:100.

Hydrous alumina ($Al_2O_3$ content of 75 weight %, SASOL Ltd.) of 33.3 g. (equivalent to $Al_2O_3$ of 25 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 15 g. synthesized similarly as in the embodiment 1 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 1.2 mmΦ holes. The extruded mold body was dried at 120° C. overnight and put under calcination at 540° C. for 2 hours after gradual elevation of temperatures from 350° C. to 540° C. The calcinated mold body of 20 g. was added to an aqueous solution in which ammonium chloride (Sigma Aldrich Corporation) of 1.65 g. and calcium chloride dihydrate (Cahc Co., Ltd.) of 2.7 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in an aqueous perrhenic acid solution (Rare Metal Production Co., Ltd.) of 30 mL containing Re of 80 mg at room temperature and left for 2 hours, while being stirred every 30 minutes. After the moisture in the mixture was removed and the mixture was dried at 120° C. overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst Q" hereinafter. Contents of calcium and sodium in the catalyst were determined by the atomic absorption spectrometry, resulting that Ca and Na were of 0.25 weight % and 0.3 weight % respectively. A quantity of rhenium supported in the catalyst was determined by ICP emission spectroscopy, resulting Re metal to be of 0.35 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 16:100.

Hydrous alumina ($Al_2O_3$ content of 75 weight %, SASOL Ltd.) of 33.3 g. (equivalent to $Al_2O_3$ of 25 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 15 g. synthesized similarly as in the embodiment 1 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 1.5 mmΦ holes. The extruded mold body was dried at 120° C. overnight and put under calcination at 540° C. for 2 hours after gradual elevation of temperatures from 350° C. to 540° C. The calcinated mold body of 20 g. was added to an aqueous solution in which ammonium chloride (Sigma Aldrich Corporation) of 1.65 g. and calcium chloride dihydrate (Cahc Co., Ltd.) of 2.7 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in an aqueous perrhenic acid solution (Rare Metal Production Co., Ltd.) of 30 mL containing Re of 80 mg at room temperature and left for 2 hours, while being stirred every 30 minutes. After the moisture in the mixture was removed and the mixture was dried at 120° C. overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst R" hereinafter. Contents of calcium and sodium in the catalyst were determined by the atomic absorption spectrometry, resulting that Ca and Na were of 0.24 weight % and 0.3 weight % respectively. A quantity of rhenium supported in the catalyst was determined by ICP emission spectroscopy, resulting Re metal to be of 0.33 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 15:100.

Hydrous alumina ($Al_2O_3$ content of 75 weight %, SASOL Ltd.) of 33.3 g. (equivalent to $Al_2O_3$ of 25 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 15 g. synthesized similarly as in the embodiment 1 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 1.7 mmΦ holes. The extruded mold body was dried at 120° C. overnight and put under calcination at 540° C. for 2 hours after gradual elevation of temperatures from 350° C. to 540° C. The calcinated mold body of 20 g. was added to an aqueous solution in which ammonium chloride (Sigma Aldrich Corporation) of 1.65 g. and calcium chloride dihydrate (Cahc Co. Ltd.) of 2.7 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in an aqueous perrhenic acid solution (Rare Metal Production Co., Ltd.) of 30 mL containing Re of 80 mg at room temperature and left for 2 hours, while being stirred every 30 minutes. After the moisture in the mixture was removed and the mixture was dried at 120° C. Overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst S" hereinafter. Contents of calcium and sodium in the catalyst were determined by the atomic absorption spectrometry, resulting that Ca and Na were of 0.23 weight % and 0.3 weight % respectively. A quantity of rhenium supported in the catalyst was determined by ICP emission spectroscopy, resulting Re metal to be of 0.32 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 15:100.

Hydrous alumina ($Al_2O_3$ content of 75 weight %, SASOL Ltd.) of 33.3 g. (equivalent to $Al_2O_3$ of 25 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 15 g. synthesized similarly as in the embodiment 1 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 0.5 mmΦ holes. The extruded mold body was dried at 120% overnight and put under calcination at 540° C. for 2 hours after gradual elevation of temperatures from 350° C. to 540° C. The calcinated mold body of 20 g. was added to an aqueous solution in which ammonium nitrate (Sigma Aldrich Corporation) of 4.94 g. and silver nitrate (Sigma Aldrich Corporation) of 2.3 g. were dissolved in distilled water of 60 g. and treated at 80° C. for 1 hour, while being stirred intermittently. After such treatment, the aqueous solution was removed and the resultant mixture was washed with distilled water and filtered repeatedly 5 times. The mixture was immersed in a perrhenic acid aqueous solution (Rare Metal Production Co., Ltd.) of 30 mL containing Re of 160 mg at room temperature and left for 2 hours, while being stirred every 30 minutes. After the moisture in the mixture was removed and the mixture was dried at 120° C. overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst S" hereinafter. Contents of silver and sodium in the catalyst were determined by the atomic absorption spectrometry, resulting that Ag and Na were of 1.7 weight % and 0.1 weight % respectively. A quantity of rhenium supported in the catalyst was determined by ICP emission spectroscopy, resulting Re metal to be of 0.67 weight %. This catalyst was ground to be measured by X-ray diffraction, and the X-ray diffraction intensity ratio of the crystal lattice spacing d-value of 0.196 nm (2θ=46.18°) to the crystal lattice spacing d-value of 0.386 nm (2θ=23.04°) was proved to be 15:100.

Catalysts from L to O were filled into reaction tubes respectively by 7.5 g., and xylenes containing ethylbenzene were put under gas phase reaction in the presence of hydrogen. Table 3 shows the result.

TABLE 3

Performance of each catalyst

| | Supplied raw material | Embodiment 27 | Embodiment 28 | Embodiment 29 | Embodiment 30 |
|---|---|---|---|---|---|
| Reaction condition | | Catalyst L | Catalyst M | Catalyst N | Catalyst O |
| Reaction temperature ° C. | | 366 | 370 | 376 | 379 |
| Reaction pressure MPa-G | | 0.64 | 0.64 | 0.64 | 0.64 |
| W/F g-cat · hr/g-mol | | 30 | 15 | 30 | 30 |
| H2/F mol/mol | | 3.5 | 3.5 | 3.5 | 3.5 |
| C1 wt % | | 0.00 | 0.01 | 0.00 | 0.00 |
| C2 | | 2.75 | 2.90 | 2.86 | 2.88 |
| C3 | | 0.10 | 0.05 | 0.06 | 0.05 |
| C4 | | 0.01 | 0.01 | 0.01 | 0.01 |
| C7- wt % | 0.01 | 0.16 | 0.10 | 0.08 | 0.05 |
| C8NP | 0.09 | 0.07 | 0.05 | 0.05 | 0.05 |
| BZ | 0.01 | 7.12 | 7.46 | 7.42 | 7.48 |
| TOL | 1.48 | 3.22 | 2.94 | 2.55 | 2.43 |
| EB | 15.21 | 3.65 | 3.80 | 3.72 | 3.80 |
| p-X | 0.86 | 19.01 | 19.19 | 19.38 | 19.00 |
| m-X | 56.89 | 42.62 | 43.07 | 43.38 | 43.26 |
| o-X | 25.37 | 19.25 | 19.44 | 19.72 | 20.34 |
| Pr-B | 0.00 | 0.00 | 0.00 | 0.00 | 0.00 |
| ET | 0.05 | 0.51 | 0.25 | 0.17 | 0.16 |
| TMB | 0.03 | 0.56 | 0.44 | 0.33 | 0.24 |
| DEB | 0.00 | 0.38 | 0.12 | 0.14 | 0.16 |
| EX | 0.00 | 0.55 | 0.08 | 0.10 | 0.07 |
| C10+ | 0.00 | 0.04 | 0.10 | 0.03 | 0.01 |
| EB conversion wt % | | 76.0 | 74.4 | 75.1 | 74.5 |
| p-X/ΣX | | 23.5 | 23.5 | 23.5 | 23.0 |
| XY loss | | 2.7 | 1.7 | 1.2 | 1.0 |

The embodiments from 27 to 30 indicate that the presence of alkaline-earth metals in the catalyst reduces xylene loss.

Embodiments from 31 to 35

Catalysts from P to T were filled into reaction tubes respectively by 2.5 g., and xylenes containing ethylbenzene were put under gas phase reaction in the presence of hydrogen. Table 4 shows the result.

TABLE 4

Performance of each catalyst

| | Supplied raw material | Embodiment 31 | Embodiment 32 | Embodiment 33 | Embodiment 34 | Embodiment 35 |
|---|---|---|---|---|---|---|
| Reaction condition | | Catalyst P | Catalyst Q | Catalyst R | Catalyst S | Catalyst T |
| Reaction temperature ° C. | | 383 | 382 | 382 | 382 | 382 |
| Reaction pressure MPa-G | | 0.64 | 0.64 | 0.64 | 0.64 | 0.64 |

TABLE 4-continued

Performance of each catalyst

| | Supplied raw material | Embodiment 31 | Embodiment 32 | Embodiment 33 | Embodiment 34 | Embodiment 35 |
|---|---|---|---|---|---|---|
| W/F g-cat · hr/g-mol | | 30 | 15 | 30 | 30 | 30 |
| H2/F mol/mol | | 3.5 | 3.5 | 3.5 | 3.5 | 3.5 |
| C1 wt % | 0.01 | 0.01 | 0.00 | 0.01 | 0.00 | |
| C2 | | 2.44 | 2.34 | 2.45 | 2.35 | 2.43 |
| C3 | | 0.05 | 0.07 | 0.06 | 0.07 | 0.06 |
| C4 | | 0.01 | 0.01 | 0.01 | 0.01 | 0.01 |
| C7− wt % | 0.00 | 0.04 | 0.05 | 0.08 | 0.05 | 0.12 |
| C8NP | 0.08 | 0.07 | 0.05 | 0.05 | 0.05 | 0.07 |
| BZ | 0.01 | 6.58 | 6.60 | 6.63 | 6.60 | 6.83 |
| TOL | 1.48 | 2.20 | 2.49 | 2.55 | 2.49 | 2.32 |
| EB | 15.15 | 5.32 | 5.26 | 5.18 | 5.37 | 5.15 |
| p-X | 0.89 | 18.97 | 18.77 | 18.09 | 17.55 | 19.18 |
| m-X | 56.87 | 43.71 | 43.61 | 43.78 | 44.02 | 43.05 |
| o-X | 25.46 | 19.79 | 19.92 | 20.35 | 20.69 | 20.04 |
| Pr-B | 0.00 | 0.00 | 0.00 | 0.00 | 0.00 | 0.00 |
| ET | 0.03 | 0.20 | 0.18 | 0.17 | 0.19 | 0.17 |
| TMB | 0.02 | 0.24 | 0.27 | 0.33 | 0.25 | 0.29 |
| DEB | 0.00 | 0.24 | 0.19 | 0.14 | 0.19 | 0.18 |
| EX | 0.00 | 0.13 | 0.08 | 0.10 | 0.11 | 0.09 |
| C10+ | 0.00 | 0.00 | 0.10 | 0.03 | 0.00 | 0.01 |
| EB conversion wt % | | 64.9 | 65.3 | 65.8 | 64.6 | 66.0 |
| p-X/ΣX | | 23.0 | 22.8 | 22.0 | 21.3 | 23.3 |
| XY loss | | 0.9 | 1.1 | 1.2 | 1.1 | 1.1 |

The embodiments from 31 to 35 indicate that the rate of isomerization to para-xylene is reduced as the diameter of the catalyst particle increase. The embodiment 35 indicates that the rate of isomerization to para-xylene increases by the introduction of silver ions.

Embodiment 36 (Preparation of Catalyst U)

Hydrous alumina ($Al_2O_3$ content of 75 weight %, SASOL Ltd.) of 33.3 g. (equivalent to $Al_2O_3$ of 25 g.) and alumina sol ($Al_2O_3$ content of 10 weight %, Nissan Chemical Industries Ltd.) of 60 g. (equivalent to $Al_2O_3$ of 6 g.) were added to MFI-type zeolite of 15 g. synthesized similarly as in the embodiment 9 on the basis of the absolute dry standard (calculated from the loss on ignition during 20-minute calcination at 500° C.) to be well mixed. Thereafter, the resultant was placed in a dryer kept at 120° C. and dried until the moisture content was reduced to that of a clay. The kneaded mixture was extruded through a screen having 1.6 mmΦ holes. The extruded mold body was dried at 120° C. overnight and put under calcination at 540° C. for 2 hours after gradual elevation of temperatures from 350° C. to 540° C. The calcinated mold body of 20 g. was added to an aqueous solution in which ammonium chloride (Sigma Aldrich Corporation) of 3.30 g. and barium nitrate (Cahc Co., Ltd.) of 1.77 g. were dissolved in distilled water of 60 g. and treated at 80 Ž for 1 hour, while being stirred intermittently. After such treatment, the aqueous solution was removed and the resultant mixture was washed with distilled water and filtered repeatedly 5 times. The mixture was immersed in a perrhenic acid aqueous solution (Rare Metal Production Co., Ltd.) of 30 mL containing Re of 160 mg at room temperature and left for 2 hours, while being stirred every 30 minutes. After the moisture in the mixture was removed and the mixture was dried at 120° C. overnight, the mixture was treated with hydrogen sulfide at 250° C. for 2 hours in a hydrogen sulfide stream, and subsequently put under calcination at 540° C. for 2 hours in the atmosphere. This catalyst is referred to as "catalyst U" hereinafter. Contents of barium and sodium in the catalyst were determined by the atomic absorption spectrometry, resulting that Ba and Na were of 0.5 weight % and 0.1 weight % respectively. A quantity of rhenium supported in the catalyst was determined by ICP emission spectroscopy, resulting Re metal to be of 0.65 weight %. This catalyst was ground to be measured by X-ray diffraction. FIG. 13 shows the result and the X-ray diffraction intensity ratio of the crystal lattice spacing d-value of 0.195 nm (2θ=46.44°) to the crystal lattice spacing d-value of 0.385 nm (2θ=23.06°) was proved to be 20:100.

Fifteen grams of the MFI-type zeolite synthesized similarly as in the embodiment 9 in accordance with the absolute dry standard (calculated on the basis of loss on ignition for 20-minute calcination at 500° C.) was added to hydrous alumina ($Al_2O_3$ content of 75% by weight, SASOL Ltd.) of 33.3 g. (25 g. as $Al_2O_3$) and of alumina sol ($Al_2O_3$ content of 10% by weight, Nissan Chemical Industries Ltd.) of 60 g. (6 g. as $Al_2O_3$) and well mixed. Thereafter, the resultant was placed in a dryer kept at 120° C. and dried until the moisture content on to that of a clay. The thus-prepared kneaded substance was extruded through a screen having 1.6 mmΦ holes. The extruded was dried overnight at 120° C. and subjected to 2-hour calcination at 540° C. after gradual elevation of temperature from 350° C. to 540° C. Twenty grams of the thus-calcinated substance was placed into an aqueous solution in which ammonium nitrate of 3.30 g. (Sigma Aldrich Corporation), barium nitrate of 3.3 g. (Sigma Aldrich Corporation) and silver nitrate of 2.3 g. (Cahc Co., Ltd.) were dissolved in distilled water of 60 g., and treated at 80° C. for 1 hour, with occasional stirring. After such treatment, the aqueous solution was removed and the resultant substance was repeatedly washed with distilled water and filtered 5 times. The substance was submerged in 30 mL of perrhenic acid aqueous solution (Rare Metal Production Co., Ltd.) containing Re of 160 mg at room temperature and allowed to stand for 2 hours. The stirring was given every 30 minutes. Then, the moisture was removed from the substance and the substance was dried overnight at 120° C. After drying, the substance was treated with hydrogen sulfide at 250° C. for 2 hours in a hydrogen sulfide atmosphere, and then subjected to 2-hour calcination at 540° C. in the air. The substance is hereinafter referred to as "catalyst V". Barium, silver and sodium contents of the catalyst were determined by atomic absorption spectrometry, resulting in a finding of 1.0% by weight as Ba, 2.7% by weight as Ag and 0.1% by weight as Na. A quantity of rhenium supported in the catalyst was determined by ICP emission spectrography analysis, resulting in a finding of 0.68% by weight as Re metal. This catalyst was ground and subjected to X-ray diffraction, resulting in a finding that the X-ray diffraction intensity ratio of the crystal lattice spacing d-value of 0.195 nm (2θ=46.44°) to the crystal lattice spacing d-value of 0.384 nm (2θ=23.12°) was 19:100.

Fifteen grams of the MFI-type zeolite synthesized similarly as in the embodiment X in accordance with the absolute dry standard (calculated on the basis of loss on ignition for 20-minute calcination at 500° C.) was added to 33.3 g. of hydrous alumina ($Al_2O_3$ content of 75% by weight, SASOL Ltd.) (25 g. as $Al_2O_3$) and 60 g. of alumina sol ($Al_2O_3$ content of 10% by weight, Nissan Chemical Industries Ltd.) (6 g. as $Al_2O_3$) and well mixed. Thereafter, the resultant was placed in a dryer kept at 120° C. and dried until the moisture content to that of a clay. The thus-prepared kneaded substance was extruded through a screen having 0.5 mm Φ holes. The extruded article was dried overnight at 120° C. and subjected to 2-hour calcination at 540° C. after gradual elevation of temperature from 350° C. to 540° C. Twenty grams of the thus-calcinated article was placed into an aqueous solution in which 1.65 g. of ammonium chloride (Sigma Aldrich Corporation) and 2.7 g. of calcium chloride dihydrate (Cahc Co., Ltd.) were dissolved in 60 g. of distilled water, and treated at 80° C. for 1 hour, with occasional stirring. After such treatment, the aqueous solution was removed and the resultant substance was repeatedly washed with distilled water and filtered 5 times. The substance was submerged in 30 mL of perrhenic acid aqueous solution (Rare Metal Production Co., Ltd.) containing 80 mg of Re at room temperature and allowed to stand for 2 hours. The stirring was given every 30 minutes. Then, the moisture was removed from the substance and the substance was dried overnight at 120° C. After drying, the substance was treated with hydrogen sulfide at 250° C. for 2 hours in a hydrogen sulfide atmosphere, and then subjected to 2-hour calcination at 540° C. in the air. The substance is hereinafter referred to as "catalyst S". Barium content and sodium content of the catalyst were determined by atomic absorption spectrometry, resulting in a finding of 0.9% by weight as Ba and 0.2% by weight as Na. A quantity of rhenium supported in the catalyst was determined by ICP emission spectrography analysis, resulting in a finding of 0.32% by weight as Re metal. This catalyst was ground and subjected to X-ray diffraction, resulting in a finding that the X-ray diffraction intensity ratio of the crystal lattice spacing d-value of 0.195 nm (2θ=46.44°) to the crystal lattice spacing d-value of 0.384 nm (2θ=23.12°) was 19:100.

Reaction tubes were filled with 2.5 grams of catalysts U through W, respectively, and ethylbenzene containing xylenes were subjected to gas-phase reaction in the presence of hydrogen, the result of which was shown in Table 5.

TABLE 5

| | Performance of each catalyst | | | |
|---|---|---|---|---|
| | Supplied raw material | Embodiment 39 | Embodiment 40 | Embodiment 41 |
| Reaction condition | | Catalyst U | Catalyst V | Catalyst R |
| Reaction temperature ° C. | | 408 | 396 | 438 |
| Reaction pressure MPa-G | | 0.64 | 0.64 | 0.64 |
| W/F g-cat.hr/g-mol | | 10 | 10 | 10 |
| H2/F mol/mol | | 3.5 | 3.5 | 3.5 |
| C1 wt % | | 0.01 | 0.01 | 0.01 |
| C2 | | 2.33 | 2.54 | 2.28 |
| C3 | | 0.05 | 0.03 | 0.05 |
| C4 | | 0.01 | 0.01 | 0.01 |
| C7-wt % | 0.02 | 0.09 | 0.06 | 0.12 |
| C8NP | 0.08 | 0.04 | 0.07 | 0.04 |
| BZ | 0.01 | 6.59 | 6.97 | 6.48 |
| TOL | 0.15 | 2.22 | 2.26 | 2.06 |
| EB | 15.19 | 5.64 | 5.20 | 5.94 |
| p-X | 0.87 | 19.31 | 19.52 | 19.44 |
| m-X | 56.84 | 43.54 | 43.35 | 43.22 |
| o-X | 25.41 | 19.50 | 19.28 | 19.85 |
| Pr-B | 0.00 | 0.00 | 0.00 | 0.00 |
| ET | 0.03 | 0.11 | 0.11 | 0.09 |
| TMB | 0.02 | 0.34 | 0.36 | 0.22 |
| DEB | 0.00 | 0.10 | 0.10 | 0.09 |
| EX | 0.00 | 0.11 | 0.11 | 0.08 |
| C10+ | 0.00 | 0.00 | 0.00 | 0.01 |
| EB conversion wt % | | 62.9 | 65.8 | 60.65 |
| p-X/ΣX | | 23.5 | 23.8 | 23.6 |
| XY loss | | 0.9 | 1.2 | 0.8 |

It was found from the embodiments 39 to 41 that the presence of barium ions and/or silver ions in the catalyst made it possible to reduce the loss of xylene, thus attaining conversion to ethylbenzene and isomerization to para-xylene at a high rate under the condition where W/F was 10 g-cat.hr/g-mol, or so called a limited quantity of the catalyst, even if zeolite had a $SiO_2/AlO_3$ mole ratio of 25 and the average crystallite size of the major axis was 0.05 micron and the minor axis was 0.05 micron.

The present invention is able to dealkylate ethylbenzene at a higher level and also reduce the loss of xylene occurring at the time of isomerization of ortho-xylene and meta-xylene into para-xylene by using the catalyst which includes MFI-type zeolite and alumina wherein the X-ray diffraction intensity ratio of the crystal lattice spacing d-value of 0.196±0.002 nm assigned to alumina to the crystal lattice spacing d-value of 0.386±0.008 nm assigned to MFI-type zeolite is in a range from 100:7 to 100:35.

Of xylene mixtures, a particularly important one from an industrial point of view is para-xylene, a raw material for synthetic fiber polyester. Ortho-xylene and meta-xylene which are xylene isomers other than para-xylene are in much less demand than para-xylene, and therefore, it is industrially important to attain conversion of these xylene isomers into para-xylene. The use of the catalyst claimed in the invention makes it possible to attain an effective dealkylation of ethylbenzene into benzene easily separable from xylenes and also isomerization of ortho-xylene or meta-xylene into para-xylene, with the loss of xylene from ethylbenzene containing xylenes kept lower.

What is claimed is:

1. A conversion catalyst for ethylbenzene containing xylenes which includes MFI-type zeolite at 15 to 80 weight parts and alumina at 20 to 85 weight parts, wherein Xray diffraction intensity ratio of the crystal lattice plane spacing d-value of 0.196±0.002 nm assigned to alumina to the crystal lattice plane spacing d-value of 0.386±0.008 nm assigned to MFI-type zeolite is in a range from 7:100 to 35:100,
   wherein a silica/alumina mole ratio of the MFI-type zeolite is less than or equal to 45, and
   wherein the catalyst contains rhenium, silver and at least any one of alkaline-earth metals selected from calcium, strontium or barium at 0.005 to 1.5 weight %, 0 to 5 weight % and 0.05 to 5 weight %, respectively, in relation to the catalyst.

2. The conversion catalyst for ethylbenzene containing xylenes according to claim 1, wherein the catalyst contains the MFI-type zeolite at 20 to 60 weight parts and the alumina at 40 to 80 weight parts.

3. The conversion catalyst for ethylbenzene containing xylenes according to claim 1, wherein the MFI-type zeolite includes the crystallite having the major axis and minor axis from 0.7 to 2.5 micron and the silica/alumina mole ratio from 30 to 45.

4. The conversion catalyst for ethylbenzene containing xylenes according to claim 2, wherein the MFI-type zeolite includes the crystallite having the major axis and minor axis from 0.7 to 2.5 micron and the silica/alumina mole ratio from 30 to 45.

5. The conversion catalyst for ethylbenzene containing xylenes according to claim 1, wherein the MFI-type zeolite includes the crystallite having the major axis and minor axis from 0.03 to 0.7 micron and the silica/alumina mole ratio from 18 to 30.

6. The conversion catalyst for ethylbenzene containing xylenes according to claim 2, wherein the MFI-type zeolite includes the crystallite having the major axis and minor axis from 0.03 to 0.7 micron and the silica/alumina mole ratio from 18 to 30.

7. The conversion catalyst for ethylbenzene containing xylenes according to claim 5, wherein the alkaline-earth metal is at least any one of substances selected from either strontium or barium.

8. The conversion catalyst for ethylbenzene containing xylenes according to claim 6, wherein the alkaline-earth metal is at least any one of substances selected from either strontium or barium.

9. The conversion catalyst for ethylbenzene containing xylenes according to claim 1, wherein the catalyst particle ranges from 0.2 to 2.0 mm in the diameter.

10. The conversion catalyst for ethylbenzene containing xylenes according to claim 1, wherein the catalyst is treated with hydrogen sulfide.

* * * * *